United States Patent
Sommazzi et al.

(10) Patent No.: US 6,596,891 B1
(45) Date of Patent: Jul. 22, 2003

(54) ACTIVATING COMPOSITION OF METALLOCENE COMPLEXES IN THE CATALYSIS OF (CO)POLYMERIZATION PROCESSES OF OLEFINS

(75) Inventors: Anna Sommazzi, S. Margherita Ligure (IT); Francesco Masi, Sant'Angelo Lodigiano (IT); Giampietro Borsotti, Novara (IT); Antonio Proto, Novara (IT); Roberto Santi, Novara (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/461,755

(22) Filed: Dec. 16, 1999

(30) Foreign Application Priority Data

Dec. 17, 1998 (IT) .......................... MI98A2718

(51) Int. Cl.⁷ ............................. C07F 5/06; C08F 4/44; C08F 4/02; B01J 31/00; B01J 37/00
(52) U.S. Cl. .......................... 556/181; 556/1; 556/186; 502/103; 502/117; 502/122; 502/125; 502/128; 526/125.7; 526/144; 526/160; 526/943
(58) Field of Search .................... 502/152, 169, 502/171, 103, 117, 122, 125, 128; 556/1, 181, 186; 526/125.7, 144, 160, 943

(56) References Cited

U.S. PATENT DOCUMENTS

| | | | | |
|---|---|---|---|---|
| 5,155,080 A | * | 10/1992 | Elder et al. ............... | 502/152 |
| 5,763,549 A | * | 6/1998 | Elder et al. ............... | 502/117 |
| 5,789,645 A | * | 8/1998 | Cox ........................... | 502/152 |
| 5,807,939 A | * | 9/1998 | Elder et al. ............... | 526/160 |
| 5,854,166 A | * | 12/1998 | Marks et al. .............. | 502/153 |
| 5,895,771 A | * | 4/1999 | Epstein et al. ............ | 502/152 |
| 6,031,145 A | * | 2/2000 | Commereuc et al. ...... | 502/169 |
| 6,121,395 A | * | 9/2000 | Turner ...................... | 526/134 |
| 6,130,302 A | * | 10/2000 | Marks et al. .............. | 502/153 |
| 6,147,174 A | * | 11/2000 | Holtcamp et al. ......... | 526/160 |
| 6,153,550 A | * | 11/2000 | Kissin ....................... | 502/117 |
| 6,187,940 B1 | * | 2/2001 | Chen et al. ................ | 502/117 |
| 6,211,111 B1 | * | 4/2001 | Chen et al. ................ | 502/152 |
| 6,218,332 B1 | * | 4/2001 | Marks et al. .............. | 502/169 |
| 6,229,034 B1 | * | 5/2001 | Marks et al. .............. | 556/1 |
| 6,239,059 B1 | * | 5/2001 | Saudemont et al. ....... | 502/152 |
| 6,274,752 B1 | * | 8/2001 | Marks et al. .............. | 502/152 |
| 6,291,614 B1 | * | 9/2001 | Chen et al. ................ | 502/152 |
| 6,387,838 B2 | * | 5/2002 | Chen et al. ................ | 502/103 |
| 6,388,114 B1 | * | 5/2002 | Marks et al. .............. | 556/1 |
| 2001/0018395 A1 | * | 8/2001 | Ward ......................... | 502/103 |
| 2002/0082369 A1 | * | 6/2002 | Holtcamp .................. | 526/129 |
| 2002/0115806 A1 | * | 8/2002 | Rodriguez ................. | 526/170 |
| 2002/0132728 A1 | * | 9/2002 | Rix ............................ | 502/152 |
| 2002/0132729 A1 | * | 9/2002 | LaPointe ................... | 502/155 |

* cited by examiner

*Primary Examiner*—Mark L. Bell
*Assistant Examiner*—J. Pasterczyk
(74) *Attorney, Agent, or Firm*—Oblon, Spivak, McClelland, Maier & Neustadt, P.C.

(57) ABSTRACT

An organometallic composition of a reaction product of a fluorinated organic compound of formula (I):

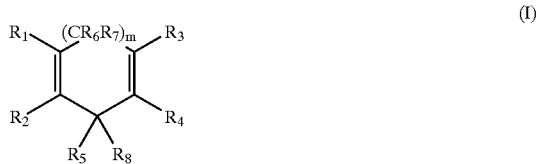

wherein $R_1$ to $R_8$ are as described in the specification, m is 0 or 1; and an organometallic compound of formula (II):

$$M'R_nX_{(p-n)} \qquad (II)$$

wherein M', R, X, n and p are as described in the specification; a polymerization catalyst composition using the above organometallic composition and a metallocene complex a method of making the catalyst composition and using the catalyst composition to polymerize α-olefins.

30 Claims, 2 Drawing Sheets

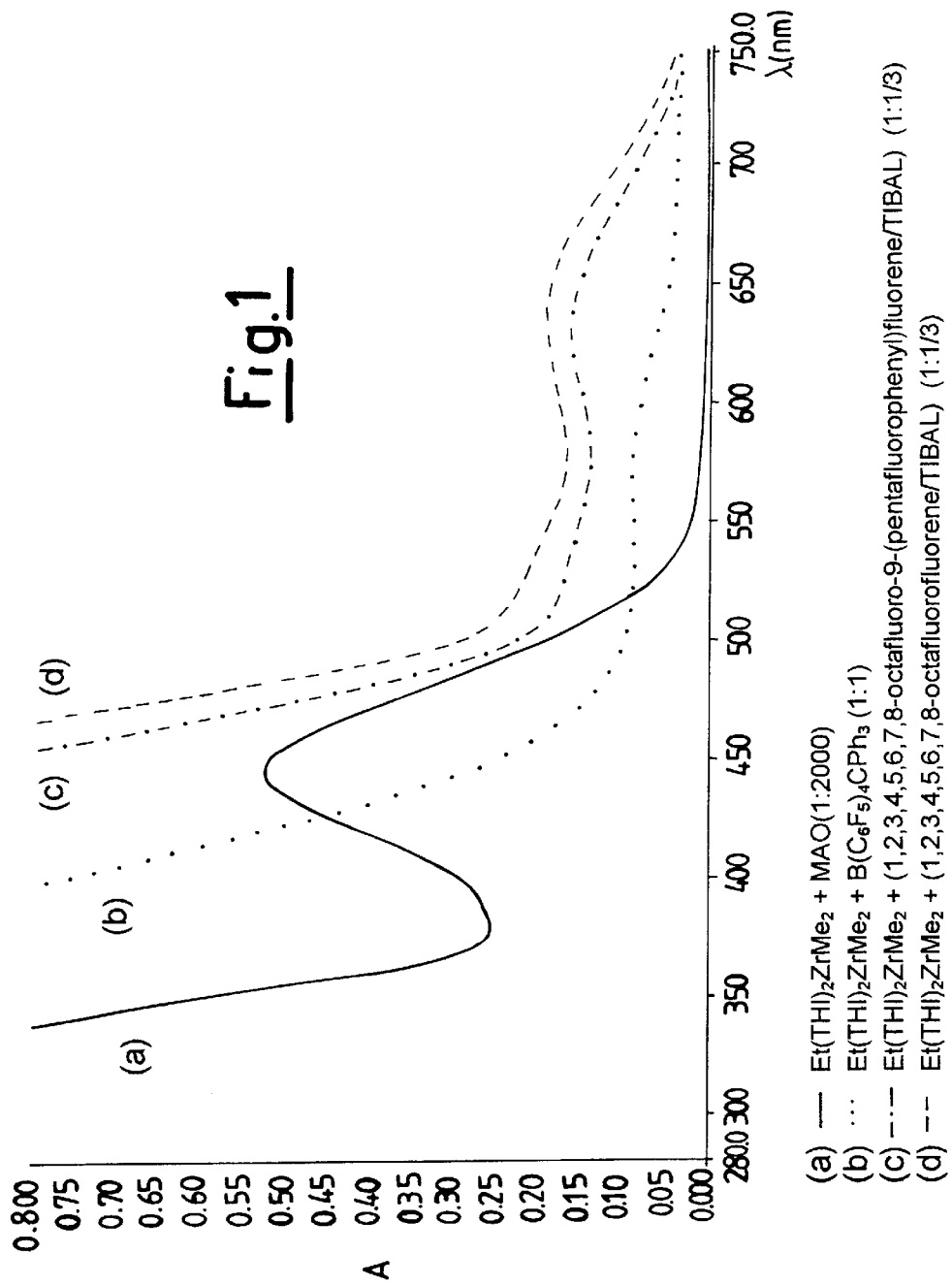

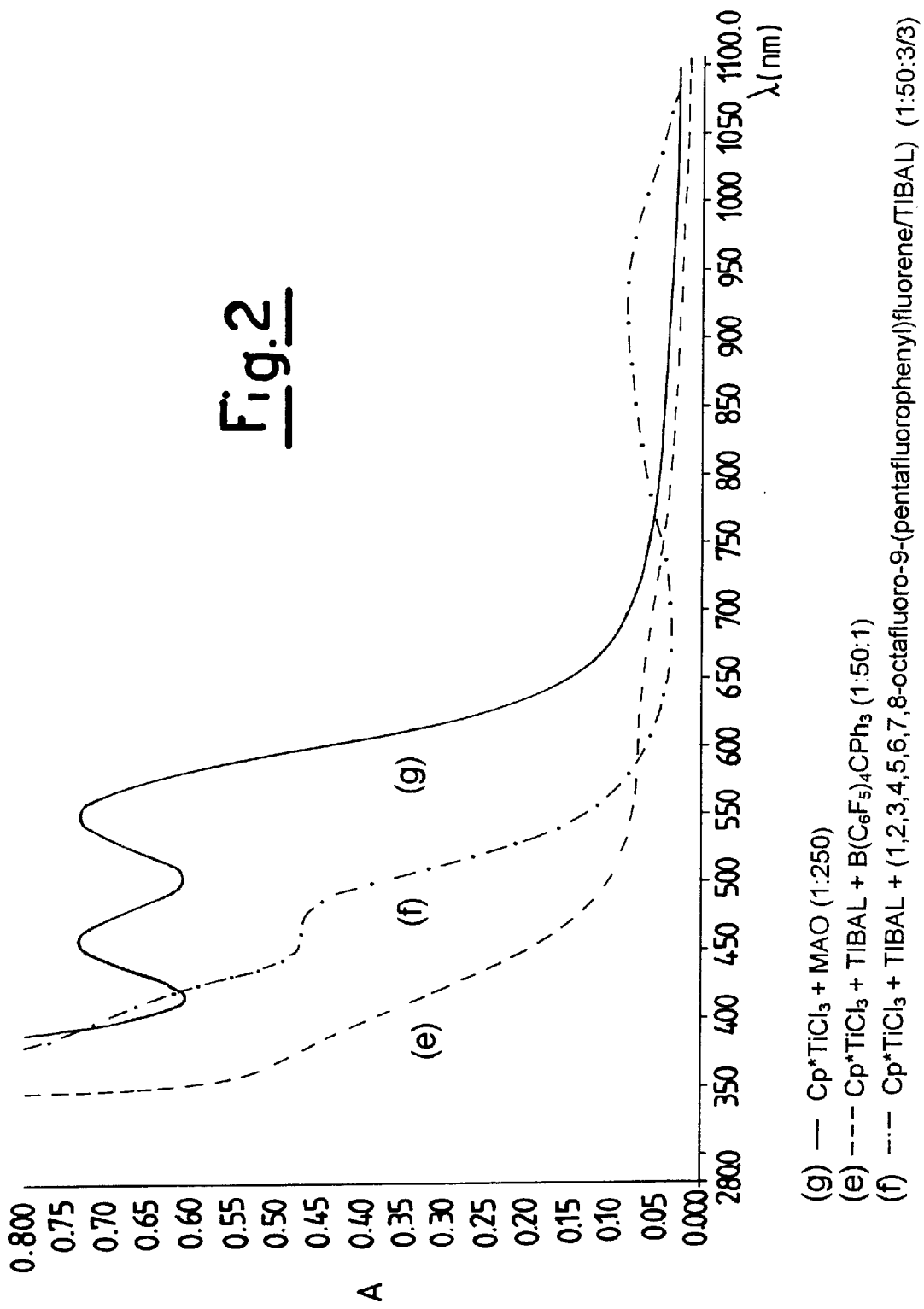

ACTIVATING COMPOSITION OF METALLOCENE COMPLEXES IN THE CATALYSIS OF (CO)POLYMERIZATION PROCESSES OF OLEFINS

The present invention relates to an activating composition of metallocene complexes in the catalysis of processes for the (co)polymerization of α-olefins.

More specifically, the present invention relates to an organometallic composition without boron and with a low content of other metals, particularly aluminum, capable of forming a catalyst with a high activity for the polymerization of α-olefins, combined with metallocene complexes of group 4 -of the periodic table of elements. The present invention also relates to said catalyst, as well as a polymerization process of α-olefins which uses it.

It is generally known in the art that ethylene, or α-olefins in general, can be polymerized or copolymerized by means of low, medium or high pressure processes with catalysts based on a transition metal. A particular group of catalysts active in the polymerization of olefins consists of the combination of an organic oxyderivative of aluminum (in particular, polymeric methylaluminoxane or MAO) with an $\eta^5$-cyclopentadienyl derivative (metallocene) of a transition metal of group 4 of the periodic table of elements (in the form approved by IUPAC and published by "CRC Press Inc." in 1989). For a known preparation technique of the above compounds, reference can be made to the description of H. Sinn, W. Kaminsky, in Adv. Organomet. Chem., vol.18 (1980), page 99 and to the U.S. Pat. No. 4,542,199.

In spite of the numerous advantages with respect to the prior known art, represented by traditional heterogeneous catalysts, of the so-called Ziegler-Natta type, having a multicentric nature, catalysts based on metallocenes have also proved to have various disadvantages which have limited their industrial development. Among these the production of polymers with an insufficient average molecular weight, especially with high temperature polymerization processes, an unsatisfactory activation rapidity of the catalytic system in processes characterized by reduced residence times in the reactor, the use of significant quantities of MAO activator and the difficulty of preparing and conserving the latter on an industrial scale, can be mentioned.

In an attempt to overcome problems in particular relating to the use of MAO, metallocene-type catalysts capable of polymerizing olefins also without aluminum compounds, or in the presence of a more limited quantity of this metal, have recently been developed. These systems however are based on the formation of a catalytic species of a cationic nature, obtained by contact of a suitable metallocene with an activator consisting of a strong Lewis acid or, more advantageously, of an organometallic salt whose anion has a delocalized charge and is weakly co-ordinating, normally a fluorinated tetra-arylborane. Various cationic systems of this type are described for example, in the publications of R. R. Jordan in "Advances in Organometallic Chemistry" vol. 32 (1990), pages 325–387, and X. Yang et al. in "Journal of the American Chemical Society", vol. 116 (1994), page 10015, which provide, in addition to a wide description of the field, numerous patent references on the matter.

The activity of cationic metallocene catalytic systems however generally lower than that, which is considerable, of systems using methylalumoxane. In addition, the known methods for the preparation of the above ionic activators based on fluoroarylboranes are complex with not completely satisfactory yields, thus further limiting the industrial use of cationic catalysts. Another disadvantage lies in the sensitivity of these ionic activators to air and humidity which makes their transfer and storage difficult.

Another aspect of the above catalysts, both ionic and those based on MAO, which is not entirely satisfactory, relates to their behaviour in the copolymerization of ethylene with α-olefins and/or dienes, to produce linear low density polyethylene or olefinic elastomers, again owing to the difficulty of obtaining copolymers with sufficiently high molecular weights, suitable for their multiple industrial applications. The necessity is known, in fact, of operating with high quantities of comonomer to insert the desired quantity into the copolymer, with a consequent increase in the chain transfer reaction rate, which is competitive with the polymerization, and production of unsatisfactory molecular weights. This drawback becomes even more critical when operating with high temperature polymerization processes in which the chain transfer reaction is already significant without the comonomer.

Other cationic systems based on metallocenes and fluoroaryl aluminates are described in international patent application WO 98/0715, which claims a higher catalytic activity. These catalysts however are relatively complex to prepare and are particularly unstable to air and humidity, similarly to those containing boro-anions and are not easily adaptable to non-alkylated metallocene complexes.

The Applicant has now found a new group of activators of metallocene complexes, suitable for forming (co)polymerization catalysts of α-olefins with a high activity and without the above disadvantages. These activators are based on certain extensively fluorinated di-unsaturated cyclic compounds, and allow the preparation of high activity catalysts with a low aluminum content. In particular, they can be prepared at the moment of use starting from precursors obtained with processes analogous to known and relatively simple processes, which are stable to air and humidity, thus solving the problem of handling, transfer and storage.

A first object of the present invention therefore relates to an organometallic composition which can be used as activator of a metallocene complex of a metal of group 4 to form a (co)polymerization catalyst of α-olefins, characterized in that it comprises the reaction product between:

(A) a fluorinated organic compound, comprising at least one di-unsaturated cycle with 5 or 6 carbon atoms, having the following formula (I):

wherein: each $R_i$ group (i being an integer from 1 to 7) is a substituent of the di-unsaturated cycle independently selected from hydrogen, fluorine and a fluorinated or non-fluorinated, aliphatic or aromatic hydrocarbyl group, having from 1 to 20 carbon atoms, optionally joined to a different $R_i$ hydrocarbyl group to form a further cycle, on the condition that at least two, preferably at least three, of the groups $R_1$, $R_2$, $R_3$ $R_4$ or $R_5$ are is independently selected from the group consisting of:
  fluorine, or
  a fluorinated alkyl group having the formula —CF$(R_9R_{10})$, wherein each $R_9$ or $R_{10}$ group can have any of the above meanings of the $R_i$ groups and at least one of them is fluorine, or fluorinated alkyl at least in position 1, or a fluorinated aryl $Ar_F$ as defined below, or a fluorinated vinyl group $V_F$ as defined below, or a fluorinated aryl group $Ar_F$ substituted on the aromatic ring with at least two groups selected from fluorine, a $-CF(R_9R_{10})$ group as defined above or a different $Ar_F$ group, or a fluorinated vinyl group $V_F$ substituted on at least two positions of the double bond with groups selected from fluorine, a $-CF(R_9R_{10})$ group or an $Ar_F$ group as defined above;

the $R_8$ group is hydrogen, $-OH$, $-SH$, or, together with said $R_5$ group, it forms a carbonyl oxygen; and "m" can have the values of 0 or 1;

(B) an organometallic compound having the following formula (II):

$$M'R_nX_{(p-n)} \quad (II)$$

wherein: M' is a metal of group 2 or 13 of the periodic table of elements, preferably Mg or Al, more preferably Al, each R is independently a hydrocarbyl, preferably alkyl, group having from 1 to 10 carbon atoms, each X is a halogen atom, preferably chlorine or bromine, "p" is the valence of M' and is equal to 2 for group 2 and 3 for group 13, "n" is a decimal number ranging from 1 to p, preferably p.

A second object of the present invention relates to a catalytic composition active in the (co)polymerization of α-olefins comprising the following components in contact with each other:

the above organometallic composition; and a metallocene complex of a metal of group 4 of the periodic table, comprising at least one cyclopentadienyl anion optionally substituted, pentahapto($\eta^5$-)coordinated to said metal.

This complex preferably has the following formula (III):

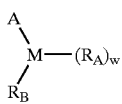

(III)

wherein:

M represents a metal of group 4, specifically Ti, Zr or Hf;

each $R_A$ independently represents a group of an anionic nature bound to the metal M, different from cyclopentadienyl or substituted cyclopentadienyl;

"w" is an Index which can have integer values 1 or 2 depending on whether the valence of M is 3 or 4;

A represents an anionic ligand having from 5 to 30 carbon atoms, comprising an $\eta^5$-cyclopentadienyl ring coordinated to the metal M;

$R_B$, regardless of the nature of the other substituents, can have any of the meanings previously specified for the ligand A and for the group $R_A$, and can also be connected with said group A by means of a divalent organic group having from 1 to 15 carbon atoms, to form a so-called "bridged" metallocene complex.

Other possible objects of the present invention will appear evident from the following description and examples.

The term "(co)polymerization of α-olefins" as used hereafter in the text and claims, refers to both the homopolymerization and copolymerization of α-olefins with each other or with another ethylenically unsaturated polymerizable compound.

Organometallic Composition

According to the present invention, the above fluorinated organic compound having formula (I) is characterized by the presence in the molecule of a di-unsaturated cycle having 5 or 6 carbon atoms, i.e. a cyclopentadienyl ring or a 1,2,4, 6-cyclohexadienyl ring, depending on whether the value of "m" in formula (I) is 0 or 1 respectively. Compounds having formula (I) with "m"=0 are preferred, however, owing to their greater activating capacity in polymerization processes of α-olefins.

Each of the groups from $R_1$ to $R_7$ which form the substituents of this di-unsaturated cycle, can, when taken singly, be hydrogen, fluorine or an aliphatic or aromatic, monovalent hydrocarbyl group, optionally fluorinated. Typical but non-limiting meanings of the groups $R_1$–$R_7$ are: hydrogen, fluorine, methyl, trifluoromethyl, ethyl, pentafluoroethyl, 2,2,2-trifluoroethyl, 1,1-difluoroethyl, heptafluoroisopropyl, 1,1-difluorohexyl, perfluorocyclohexyl, pentafluorophenyl, ortho-, meta- and para-nonafluorodiphenyl, 2,4,6-trifluorophenyl, 2,3,5-trifluorophenyl, 1,1-difluorobenzyl, heptafluorobenzyl, pentafluorophenylmethyl, 2,6-bis(trifluoromethyl)phenyl, 2,6-difluoro-4-trifluoromethylphenyl, etc. Fluoro, trifluoromethyl, pentafluorophenyl, ortho- meta- or para-bis(trifluoro-methyl)phenyl groups are preferred as fluorinated groups owing to their high activating activity and the commercial availability of the precursors of compounds having formula (I) substituted with these groups.

When two or more $R_1$–$R_7$ groups are joined to each other to form cyclic structures comprising two atoms of the di-unsaturated cycle having formula (I), these $R_i$ groups (i=1–7) are formally divalent and can be saturated or unsaturated to form saturated, unsaturated or aromatic rings, condensed with the first di-unsaturated cycle, preferably having from 5 to 8 carbon atoms, more preferably aromatic rings with 6 atoms. In this way compounds having formula (I) consisting of condensed di- or poly-cyclic structures are formed.

According to a preferred aspect of the present invention, the two groups $R_1$ and $R_2$, and optionally also the two groups $R_3$ and $R_4$ in the compound having formula (I) with "m" equal to 0, consist of fluorinated vinyl groups as defined above, which are bound to each other on the second unsaturated carbon so as to form one, or optionally two aromatic rings condensed with said di-unsaturated ring. In this way indenes or fluorenes (or the corresponding hydroxy- or thio-derivatives with $R_8$ equal to $-OH$ or $-SH$ respectively) substituted on each aromatic ring with at least two groups selected from fluorine, fluorinated alkyl or fluorinated aryl, are respectively formed, in accordance with the requisites of the compounds having formula (I).

Among these polycyclic compounds, fluorenes are particularly preferred, and especially fluorenes having from 6 to 8 fluorine atoms, however arranged on the two aromatic cycles, as well as the corresponding hydroxy- and thio-derivatives.

According to a particular embodiment, component (A) of the organometallic composition of the present invention consists of a compound having formula (I) wherein the two groups $R_5$ and $R_8$ jointly represent a carbonyl oxygen atom. Cylcopentadienones and cyclohexadienones substituted on the ring with fluorine or fluorinated groups according to what is specified above, are therefore included in the scope of formula (I).

The compound having formula (I) preferably comprises from 5 to 50 carbon atoms and from 5 to 25 fluorine atoms. More preferably, this compound is a cyclopentadiene compound ("m"=0) having from 9 to 40 carbon atoms and from 9 to 25 fluorine atoms.

For example, compounds having formula (I) with "m"=1 are perfluoro-3-hydroxycyclohexa-1,4 diene, 1,2,3,4,5,6,6-heptafluorocyclohexa-1,4-diene, 1,2,4,5-tetrakis(pentafluorophenyl)cyclohexa-1,4-diene, 1,2,4,5-tetrakis(trifluoromethyl)cyclohexa-1,4-diene, 1,2,4,5-tetrakis(pentafluorophenyl)-3-hydroxycyclohexa-1,4-diene, 9,10-dihydroperflu-oroanthracene, 9-hydroxy-9,10-dihydroperfluoroanthracene, 10,10-H,H-perfluoro-9-phenyl-9,10-dihydroanthracene, 10,10-H,H-9-hydroxyperfluoro-9-phenyl-9,10-dihydroanthracene.

Typical examples of fluorinated compounds having formula (I) with "m"=0 are fluorinated cyclopentadienes with at least three fluorine atoms on the ring, or, cyclopentadienes substituted with trifluoromethyl groups. Also included in the scope of formula (I) are derivatives of cyclopentadiene condensed with one or two extensively fluorinated aromatic rings, such as hexafluoro indene or octafluoro-fluorene. Other examples of compounds having formula (I) are indenes and fluorenes hydrogenated on the aromatic rings such as 4,4,7,7-tetrafluoro-4,5,6,7-tetrahydroindenes substituted with at least two fluorine atoms or two pentafluorophenyl groups on the cyclopentadienyl ring, and 1,1,4,4,5,5,8,8-octafluoro-1,2,3,4,5,6,7,8-octahydrofluorenes and the corresponding compounds substituted with a pentafluorophenyl group in position 9. In addition to these fluorinated hydrocarbon compounds, the corresponding hydroxy- and thio-derivatives substituted with an —OH or —SH group on the saturated position of the cyclopentadienyl ring, are typical examples of compounds included in formula (I)

According to a preferred embodiment of the present invention, in the compounds having formula (I) "m" is equal to 0 and $R_5$ is selected from fluorine, pentafluorophenyl, nonafluorodiphenyl, bis(trifluoromethyl)phenyl and tris (trifluoromethyl)phenyl.

According to another embodiment of the present invention, 1,2,3,4,5,6,7,8-octafluorofluorenes wherein $R_6$ is hydrogen or hydroxy and $R_5$ is fluorine, trifluoromethyl, pentafluorophenyl or bis(trifluoromethyl)phenyl, are preferred as compounds having formula (I).

Further, specific and non-limiting examples of said compounds having formula (I) are: 1,2,4-tris-(pentafluorophenyl)cyclopentadiene, 1,2,3-tris-(pentafluorophen-yl)cyclopentadiene, 1,2,3,4-tetrakis (pentafluorophenyl)-cyclopentadiene, 1,2,3,4,5,6,7,8-octafluorofluorene, 1,2,3,4,5,6,7,8-octafluoro-9-hydoxy-9-(2,4-bis-trifluoro-methyl-phenyl)fluorene, 1,2,3,4,5,6,7,8-octafluoro-9-(2,4-bis-trifluoromethylphenyl)fluorene, 1,2,3,4,5,6,7,8-octa-fluoro-9-hydroxy-9-(3,5-bis-trifluoromethylphenyl)fluorene, 1,2,3,4,5,6,7,8-octafluoro-9-(pentafluorophenyl)fluorene, 1,2,3,4,5,6,7,8-octafluoro-9-hydroxy-9-(pentafluorophenyl)-fluorene, 1,2,3,4,5,6,7,8-octafluoro-9-hydroxy-9-(nonaflu-orodiphenyl)fluorene, 1,2,3,4,5,6,7,8-octafluorofluoren-9-one.

Mixtures of these cyclic compounds having formula (I) are equally suitable as component (A) of the organometallic compositions of the present invention.

Some of the compounds included in formula (I) are known in literature and their synthetic methods are described. For example pentafluorocyclopentadiene, octafluorofluorene, octafluoro-9-hydroxyfluorene, 9-pentafluorophenyloctafluorofluorene, 2,3,4,5-tetrakis (trifluoromethyl)-1-hydroxycyclopentadiene, 1,2,3,4,5-pentakis-(trifluoromethyl)-cyclopentadiene, 1,4-bis(pentafluorophe-nyl)cyclopentadiene, 10,10-H,H-perfluoro-9-phenyl-9,10-di-hydroanthracene. As far as the Applicant knows, the use of these compounds and others having formula (I) which are not known, in the formation of an activating organometallic composition such as that object of the present invention, has never been disclosed or suggested.

In particular, the fluorinated cyclopentadiene compounds having formula (I) and having the following formula (IV) are new and form a further object of the present invention:

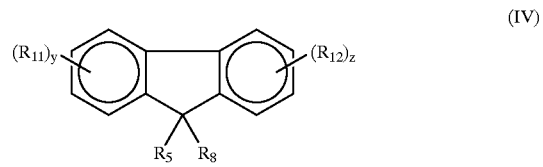

(IV)

wherein:
$R_5$ and $R_6$ have the same meaning defined for formula (I);
(y) is an integer from 1 to 4;
(z) is an integer from 1 to 4;
the groups $R_{11}$ and $R_{12}$ are independently substituents of hydrogen atoms of the respective aromatic ring in one or more of the four positions available, and are selected from fluorine or a fluorinated or non-fluorinated, aliphatic or aromatic hydrocarbyl group, having from 1 to 20 carbon atoms, optionally joined to a different $R_{11}$ or $R_{12}$ hydrocarbyl group, respectively, to form another cycle,
on the condition that at least 3, preferably at least 4, of the groups $R_5$, $R_{11}$ and $R_{12}$ are independently selected from the group consisting of:
fluorine, or a fluorinated alkyl group having the formula —$CF(R_9R_{10})$ wherein each $R_9$ or $R_{10}$ group can have any of the above meanings of $R_i$ groups and at least one of these is fluorine, or fluorinated alkyl at least in position 1, or a fluorinated aryl $Ar_F$ as defined below, or a fluorinated vinyl group $V_F$ as defined below, or
a fluorinated aryl $Ar_F$ substituted on the aromatic ring with at least two groups selected from fluorine, a —$CF(R_9R_{10})$ group as defined above or a different $Ar_F$ group, or
a fluorinated vinyl group $V_F$ substituted on at least two positions of the double bond with groups selected from fluorine, a —$CF(R_9R_{10})$ group or an $Ar_F$ group as defined above;
and in addition, $R_5$ is different from H and, if $R_8$ is H, $R_5$ is different from pentafluorophenyl.

In a preferred embodiment, in the compounds having formula (IV), all the eight $R_{11}$ and $R_{12}$ are equal to each other and are trifluoromethyl or, even more preferably fluorine.

The above compounds having formula (I), even if new, can generally be obtained by adopting for the purpose the usual synthetic methods of organic chemistry, using the specific precursors and known reactions which the average expert in the field is capable of identifying on the basis of the structure of the desired compound. Examples of specific processes are described by R. Filler et al., in the publication "Journal of Organic Chemistry", vol. 45 (1980); page 1290; by Vlasov V. M. et al. in the publication reviewed in "Chemical Abstract" vol. 90 (1979), Nr.90:86522q; by Mark J. B. et al. in "Journal of the American Chemical Society", vol. 113 (1991), pages 2209–2222; by P. a. Deck et al. in "Organometallics" vol. 15 (1996), pages 5287–5291; by V. M. Vlasov in "Journal of Fluorine Chemistry" vol. 9 (1977), pages 321–325.

According to a particular process set up by the Applicant, octafluorene-9-hydroxy fluorenes substituted in position 9 with an alkyl or fluorinated aryl group can be obtained starting from perfluorofluorenone by the reaction with an equivalent quantity (about 1/1 in moles) of a lithium derivative having the formula $R_5Li$ (with $R_5$ alkyl or fluorinated aryl having from 1 to 20 carbon atoms, preferably trifluoromethyl, pentafluoroethyl, pentafluorophenyl and bis (trifluoromethylphenyl), in a solution of a hydrocarbon solvent, preferably at temperatures ranging from −50 to +20° C., followed by hydrolysis.

The corresponding octafluorofluorenes can be obtained from the hydroxy derivatives by the bromination reaction of the hydroxyl group with a suitable brominating agent such as $PBr_3$, optionally followed by reduction by means of zinc or another reducing agent of the bromide group, to give the corresponding fluorinated hydrocarbon. In the specific case that "y" and "z" are both 4, $R_{11}$ and $R_{12}$ are F and $R_5$ in formula (IV) is 3,5-bis(trifluoromethyl)phenyl, it is not necessary to have any reduction step according to this preparative process.

Component (B) of the activating organometallic composition of the present invention consists, in its most general sense, of an alkyl compound of a metal of groups 2 or 13 of the periodic table, preferably Mg or Al, more preferably Al. This compound can also contain halogen atoms, especially chlorine, as well as the alkyl part. Non-limiting examples of these compounds are: Grignard reagents such as methylmagnesium chloride, ethylmagnesium chloride, octylmagnesium chloride and phenylmagnesium chloride; magnesium dialkyls such as magnesium diethyl, magnesium dibutyl, etc; aluminum alkyls and aluminum alkyl halides such as aluminum triethyl, aluminum tri-isobutyl, aluminum tri n-hexyl, aluminum tri-n-octyl, aluminum isoprenyl, aluminum diethylchloride, aluminum dibutylchloride, aluminumethyl sesquichloride, aluminum di-iso-butyl chloride and aluminum di-n-octyl chloride, aluminum triisoprenyl or their mixtures. Many of these organometallic compounds are known in the art and some are commercially available.

Aluminum alkyls which are particularly suitable as component (B) are aluminum trialkyls in which "n" in formula (II) is 3 and the three alkyl groups are equal to each other and have from 2 to 6 carbon atoms, such as aluminum triethyl, aluminum tributyl, aluminum tri-n-hexyl, aluminum tri-isobutyl or mixtures of these.

These aluminum alkyls are commercial products or can in any case be obtained by means of the known preparative methods in organometallic chemistry.

In the activating organometallic composition of the present invention, the two components (A) and (B) are preferably present in molar ratios (B)/(A) ranging from 0.1 to 100. It has been found that the use of molar ratios (B)/(A) greater than 100 does not give any particular advantage to the catalytic system but is inconvenient as it increases the total quantity of aluminum which remains in the olefinic polymer at the end of the polymerization. Particularly preferred molar ratios (B)/(A) range from 1.0 to 10.

With reference to the quantity of component (B) effectively used for the preparation of the catalytic systems of the present invention, it should be pointed out that this can vary considerably in relation to various parameters associated with the subsequent use of the activating composition of the present invention. In particular, as can be seen hereunder, aluminum and magnesium alkyls having formula (II), especially aluminum trialkyls, can be used to a varying degree also for favouring the activation of the metallocene complex having formula (III), when the $R_A$ groups are different from alkyl or aryl, or, according to what is already known in the art (for example in "Journal of Polymer Science, part A", vol. 32 (1994), pages 2387–2393), as "scavenger" to guarantee the removal or deactivation of poisoning impurities of the catalytic system possibly present in the reactor or polymerization solvent and monomers themselves. The portions of component (B) used in the different preparation phases of the catalyst and polymerization process contribute to determining the total quantity of metal of group 2 or 13, especially aluminum or magnesium, contained in the olefinic polymer obtained at the end of the polymerization, and represent a critical parameter, which as a rule should be as low as possible to give the polymer itself the desired dielectric properties for insulating applications and to avoid food contamination.

In addition, as will be described in more detail further on, in the formation of the catalytic composition of the present invention (activating organometallic composition+ metallocene complex), it is possible both to pre-activate a chlorinated metallocene complex, for example with an aluminum alkyl, before contact with the actual activating composition itself, and to contemporaneously put the three compounds having formula (I), (II) and (III) respectively, in contact with each other in the suitable proportions. In this case, component (B) having formula (II) can be conveniently dosed in a greater quantity if the metallocene complex is chlorinated, in a lower quantity if the metallocene complex is alkylated.

With reference to the present invention, the quantities of said component (B) as a ratio of component (A), specified in the present description and claims, do not comprise the metal alkyl having formula (II), usually an aluminum trialkyl, optionally used as "scavenger", which is normally introduced into the final preparation phase of the polymerization reactor, with concentrations ranging from 0.5 to 1 mmoles/l with respect to the volume of the polymerization mixture.

The activating organometallic composition according to the present invention is preferably prepared in a suitable hydrocarbon solvent, in an inert atmosphere, normally nitrogen or argon, by contact with components (A) and (B) in the desired proportions. The reaction between the two components occurs rapidly within a wide temperature range. The two components (A) and (B) can also be put in contact with each other in the presence of a metallocene complex having formula (III) in order to obtain the formation of a catalytic composition according to the present invention, in a single step.

The Catalytic Composition

The metallocene complex having formula (III) which forms component (ii) of the catalytic composition of the present invention can comprise both a single cyclopentadienyl ligand A, and two cyclopentadienyl ligands when $R_8$ has this meaning.

In any case, the non-cyclopentadienyl $R_A$ and $R_B$ groups are preferably selected from hydride, halide, more preferably chloride or bromide, a hydrocarbyl or halogenated hydrocarbyl radical having from 1 to 30, preferably from 1 to 10, carbon atoms, different from cyclopentadienyl, a phosphonate, sulfonate or carbonate group, an alkoxy, carboxy or aryloxy group having from 1 to 20, preferably from 1 to 10, carbon atoms, an amide group, an organic group having from 1 to 20, preferably from 1 to 10, carbon atoms, bound to the metal M with an amide nitrogen atom, an organic group having from 1 to 20, preferably from 1 to 10, carbon atoms, bound to the metal M with a silicon atom.

Complexes having formula (III) wherein $R_B$ is different from cyclopentadiene are known in the art as monocyclopentadienyl complexes. A particular group of these complexes is that of the so-called "constrained metallocenes", in which the $R_B$ group, preferably an alkyl, alkylsilyl or alkylamide group, is bridge-bound with the single cyclopentadienyl group of the complex. These complexes are described for example in published patent applications EP-A 420,436, EP-A 418,044, EP-A 416,815.

Complexes of metals of group 4 comprising two cyclopentadienyl ligands, which are suitable as component (ii) in accordance with the present invention, are for example those represented by the following formula (V):

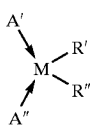

(V)

wherein:
M represents a metal selected from titanium, zirconium or hafnium;
each A' or A" independently represents an organic group containing an $\eta^5$-cyclopentadienyl ring of an anionic nature, coordinated to the metal M;
each R' or R" independently represents a group of an anionic nature σ-bound to the metal M, preferably selected from hydride, halide, a $C_1$–$C_{20}$ alkyl or alkylaryl group, a $C_3$–$C_{20}$ alkylsilyl group, a $C_5$–$C_{20}$ cycloalkyl group, a $C_6$–$C_{20}$ aryl or arylalkyl group, a $C_1$–$C_{20}$ alkoxyl or thioalkoxyl group, a $C_2$–$C_{20}$ carboxylate or carbamate group, a $C_2$–$C_{20}$ dialkylamide group and a $C_4$–$C_{20}$ alkylsilylamide group.

According to the present invention, in particular, the groups R' and R" having formula (V) each independently represent a group of an anionic nature σ-bound to the metal M. Typical examples of R' and R" are hydride, halide, preferably chloride or bromide, a linear or branched alkyl group such as methyl, ethyl, butyl, isopropyl, isoamyl, octyl, decyl, benzyl, an alkylsilyl group such as, for example, trimethylsilyl, triethylsilyl or tributylsilyl, a cycloalkyl group such as cyclopentyl, cyclohexyl, 4-methylcyclohexyl, an aryl group such as phenyl or toluyl, an alkoxyl or thioalkoxyl group such as methoxyl, ethoxyl, iso- or sec-butoxyl, ethylsulfide, a carboxylate group such as acetate, trifluoroacetate, propionate, butyrate, pivalate, stearate, benzoate, or again, a dialkylamide group such as diethylamide, dibutylamide, or alkylsilyl-amide group such as bis (trimethylsilyl)amide or ethyltrimethylsilylamide. The two groups R' and R" can also be chemically bound to each other and form a cycle having from 4 to 7 atoms different from hydrogen, also comprising the metal M. Typical examples of this aspect are divalent anionic groups such as the trimethylene or tetramethylene group, or the ethylene-dioxy group. R' and R" groups which are particularly preferred for their accessibility and the easy preparation of the complexes comprising them, are chloride, methyl and ethyl.

According to the present invention, each group of an anionic nature A in formula (III) and A' or A" in formula (V), contains an $\eta^5$-cyclopentadienyl ring coordinated to the metal M, which formally derives from a molecule of cyclopentadiene, substituted or non-substituted, by the extraction of an $H^+$ ion. The molecular structure and typical electronic and coordinative configuration of metallocene complexes of titanium, zirconium or hafnium generally comprising two $\eta^5$-cyclopentadienyl groups, is widely described in literature and is known to experts in the field.

In the more general form of the present invention, a divalent organic group, preferably containing from 1 to 20 carbon atoms, and optionally also one or more heteroatoms selected from silicon, germanium and halogens, can be bound to any of the carbon atoms of the cyclopentadienyl ring of groups A' and A" having formula (V) respectively (provided a bond valence is available).

Preferred A' and A" groups are the known cyclopentadienyl, indenyl or fluorenyl groups and their homologous products, wherein one or more carbon atoms of the molecular skeleton (included or not included in the cyclopentadienyl ring), are substituted with a radical selected from the group consisting of halogen, preferably chlorine or bromine, a linear or branched alkyl group having from 1 to 10 carbon atoms, optionally halogenated, such as methyl, trifluoromethyl, ethyl, butyl, isopropyl, isoamyl, octyl, decyl, benzyl, an alkylsilyl group such as, for example, trimethylsilyl, triethylsilyl or tributylsilyl, a cycloalkyl group such as cyclopentyl, cyclohexyl, 4-methylcyclohexyl, an aryl group having from 6 to 10 carbon atoms, optionally halogenated, such as phenyl, pentafluorophenyl or toluyl, an alkoxyl or thioalkoxyl group such as methoxyl, ethoxyl, iso- or sec-butoxyl, ethylsulfide, or again, a dialkylamide group, such as diethylamide, dibutylamide, or alkylsilyl-amide group such as bis (trimethylsilyl)amide or ethyltrimethylsilylamide. These A' or A" groups can also comprise several condensed aromatic rings, as in the case, for example, of 4,5-benzoindenyl. Particularly preferred A' or A" groups are cyclopentadienyl, indenyl, 4,5,6,7-tetra-hydroindenyl, fluorenyl, azulenyl and the corresponding methyl substituted groups.

Typical examples of complexes having formula (III) and/or (V) suitable for the purposes of the present invention are the compounds listed below, which however in no way limit the overall scope of the present invention.

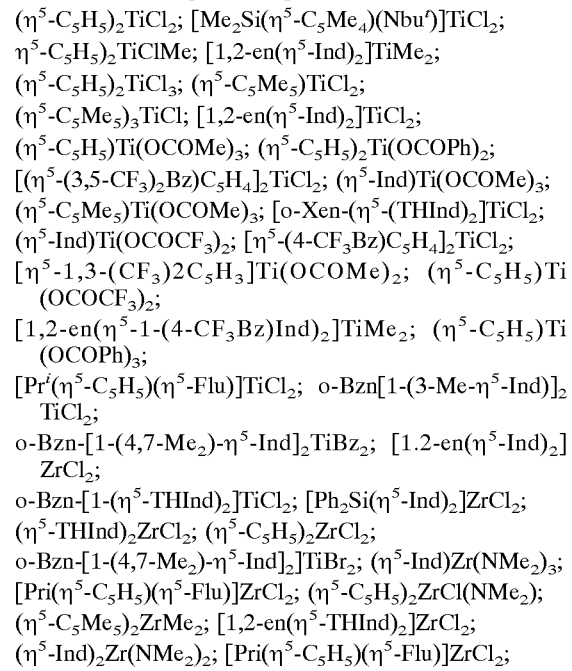

($\eta^5$-C$_5$H$_5$)$_2$ZrCl(NMe$_2$); [Me$_2$Si($\eta^5$-Ind)$_2$]HfCl$_2$;
($\eta^5$-C$_5$Me$_5$)$_2$ZrCl$_3$; o-Bzn-[1-(4,7-(Me)$_2$Ind)]$_2$ZrCl$_2$;
[o-Xen($\eta^5$-Ind)$_2$]ZrCl$_2$; ($\eta^5$-C$_5$Me$_5$)Zr(OCOPh)$_3$;
($\eta^5$-C$_5$Me$_5$)$_2$ZrBz$_2$; [1,2-en($\eta^5$-1-(2,4-(CF$_3$)$_2$Bz)Ind)$_2$]ZrCl$_2$;
[$\eta^5$-(2,4-(CF$_3$)$_2$Bz)C$_5$H$_4$]$_2$ZrCl$_2$; [Me$_2$Si(CH$_2$-$\eta^5$-C$_5$H$_4$)$_2$]ZrCl$_2$;
[o-Xen-($\eta_5$-C$_5$H$_5$)$_2$]ZrCl$_2$; ($\eta^5$-THInd)$_2$Zr(OCOCF$_3$)$_2$;
[o-Xen-($\eta^5$-THInd)$_2$]ZrCl$_2$; [o-Xen-($\eta^5$-THInd)$_2$]ZrBz$_2$;
[$\eta^5$-(2,4-(CF$_3$)$_2$Bz)C$_5$H$_4$]$_2$ZrCl(NMe$_2$); [o-Xen($\eta^5$-C$_5$H$_5$)$_2$]ZrMe$_2$;
[o-Xen-($\eta^5$-C$_5$H$_5$)($\eta^5$-Flu)]ZrCl$_2$; [$\eta^5$-(4-F—Ph)C$_5$H$_4$]$_2$ZrCl$_2$;
($\eta^5$-C$_5$Me$_5$)$_2$ZrCl$_2$; [Me$_2$Si(CH$_2$)$_2$-($\eta^5$-Ph—C$_5$H$_3$)$_2$]ZrCl$_2$;
o-Bzn[1-(5,6-(Me)$_2$Ind)]$_2$ZrCl$_2$; [1,2-en($\eta^5$-THInd)$_2$]ZrMe$_2$;
o-Bzn-[1-(4,7-diphenyl)-$\eta^5$-Ind]$_2$ZrMe$_2$; o-Bzn-(Flu)$_2$HfCl;
o-Bzn[1-(-$\eta^5$-THInd)$_2$]ZrCl$_2$; o-Bzn-[$\eta^5$-C$_5$Me$_4$]$_2$ZrCl$_2$;
o-Bzn-[1(3-Me)-$\eta^5$-Ind]$_2$HfCl$_2$; [Me$_2$Si($\eta^5$-C$_5$H$_4$)$_2$]HfCl$_2$;
o-Bzn[1-$\eta^5$-Ind)$_2$Zr(OCO-n-C$_3$H$_7$)$_2$; [Me$_2$Si($\eta^5$-(1-Ind)$_2$]HfCl$_2$;
[Me$_2$Si($\eta^5$-THInd)$_2$]HfCl$_2$; o-Bzn-[1-$\eta^5$-(3-Me)Ind]$_2$HfCl$_2$;

The following abbreviations are used in the above formulae: Me=methyl, Et=ethyl, Bu$_t$=tert-butyl, Bz=benzyl, Pr$_i$=2,2-isopropylidene, Ind=indenyl, THInd=4,5,6,7-tetrahydro-indenyl, Flu=fluorenyl, 1,2-en=1,2-ethylidene, Ph$_2$Si=diphenylsilylene, Me$_2$Si=dimethylsilylene, o-Xen=ortho-xylylene, o-Bzn=ortho-benzylidene.

The catalytic composition according to the present invention comprises, and is obtained, by contact of the above components (i) and (ii). The selection of the metallocene component (ii) can be made each time by experts in the field on the basis of optimization criteria and industrial design, with reference to the specific characteristics of the metallocene complexes in relation to the various polymerization process parameters to be obtained.

Also included in the scope of the present invention are those catalytic compositions comprising two or more complexes having formula (III) or (V) mixed with each other. Catalytic compositions of the present invention based on mixtures of metallocene complexes having different catalytic behaviour can, for example, be advantageously used in polymerization, when a wider molecular weight distribution of the polyolefins thus produced, is desired.

When the metallocene complex having formula (III) does not comprise sufficiently reactive R$_A$ groups, such as for example alkyl or aryl, it is preferable, according to the present invention, to add to the catalytic composition object thereof, a sufficient quantity of organometallic compound having formula (II) capable of also acting as alkylating agent of said complex having formula (III). The compound having formula (II), more preferably an aluminum alkyl, can be added as a separate portion to the metallocene complex to form component (ii) of the catalytic composition, in a ratio M'/M ranging from 1 to 10, preferably from 3 to 10, using a different portion for the formation of the activating organometallic composition (i), according to what is described above.

Alternatively, the whole compound having formula (II), also comprising the alkylating portion of the metallocene complex, can be put in contact with the fluorinated compound having formula (I) or with the metallocene complex having formula (III) and the product thus obtained is subsequently reacted with the missing component to form the catalytic composition of the present invention.

According to another aspect of the present invention, in order to produce solid components for the formation of polymerization catalysts of olefins, for example for use in polymerization in gas phase, the above complexes can also be supported on inert solids, preferably consisting of oxides of Si and/or Al, such as, for example, silica, alumina or silicoaluminates, but if necessary also of a polymeric nature, such as certain known polystyrenes functionalized for the purpose. The known supporting techniques can be used for the supporting of these catalysts, normally comprising contact, in a suitable inert liquid medium, between the carrier, optionally activated by heating to temperatures of over 200° C., and one or both of components (i) and (ii) of the catalyst of the present invention. It is not necessary, for the purposes of the present invention, for both components to be supported, as only the complex having formula (III), or the activating composition which forms component (i), can be present on the surface of the carrier. In the latter case, the component which is missing on the surface is subsequently put in contact with the supported component, at the moment when the catalyst active for polymerization is to be formed.

Also included in the scope of the present invention are complexes, and the catalytic compositions based thereon, which have been supported on a solid by means of the functionalization of the latter and formation of a covalent bond between the solid and a metallocene complex included in the previous formula (III).

As well as the two components (i) and (ii), one or more additives or components can be optionally added to the catalytic composition of the present invention, according to what is known in normal practice of the polymerization of olefins, to obtain a catalytic system suitable for satisfying specific requisites in the field. The catalytic systems thus obtained should be considered as being included in the scope of the present invention. Additives or components which can be included in the preparation and/or formulation of the catalytic composition of the present invention are inert solvents, such as, for example, aliphatic and/or aromatic hydrocarbons, weakly coordinated additives selected, for example, from non-polymerizable olefins or particular fluorinated ethers, halogenating agents such as silicon halides, halogenated hydrocarbons, preferably chlorinated, etc., and again all other possible components normally used in the art for the preparation of traditional homogeneous catalysts of the metallocene type for the (co)polymerization of α-olefins.

Components (i) and (ii) form the catalytic composition of the present invention by contact with each other, preferably in an inert diluent and at a temperature ranging from room temperature to the temperature selected for the polymerization which can also be, in certain processes, 150° C. or higher, and for times varying from 10 seconds to 1 hour, more preferably from 1 to 30 minutes. Inert diluents suitable for the purpose are, for example, aliphatic and aromatic hydrocarbons liquid at room temperature.

The relative quantities between the two components of the present catalytic composition are selected so that the molar ratio (A)/(M), wherein (M) are the moles of metallocene complex having formula (III) and (A) the moles of fluorinated compound having formula (I), ranges from 0.5 to 50, preferably from 1 to 10. For ratio values higher than 50 there are no significant variations in the results obtained in polymerization processes.

It has been systematically observed that the catalytic composition in accordance with the present invention has a characteristic form of the ultraviolet spectrum, with a peak at much higher wave lengths, normally of at least 50 nm, with respect to the characteristic peak observed in the ultraviolet spectra of typical ionic metallocene catalysts obtained using the known activators based on tetrakis (pentafluorophenyl)boranes combined with the same metallocene complex.

FIGS. 1 and 2 of the present patent application indicate, for illustrative purposes, the ultraviolet spectra (A absorbance of various catalytic compositions obtained by contact and reaction at room temperature, in toluene as solvent, of the following components:

BRIEF DESCRIPTION OF THE FIGURES

FIG. 1

(a) 1,2-ethylenebis(4,5,6,7-tetrahydroindenyl) zirconiumdimethyl/MAO (supplier Witco)(Al/Zr= 2000):

(b) 1,2-ethylenebis(4,5,6,7-tetrahydroindenyl) zirconiumdimethyl/B($C_6F_5$)$_4$CPh$_3$ (B/Zr=1/1);

(c) 1,2-ethylenebis(4,5,6,7-tetrahydroindenyl) zirconiumdimethyl/1,2,3,4,5,6,7,8-octafluoro-9-(pentafluorophenyl)fluorene/TIBAL (Zr/fluorene/Al= 1/1/0.33);

(d) 1,2-ethylenebis(4,5,6,7-tetrahydroindenyl) zirconiumdimethyl/1,2,3,4,5,6,7,8-octafluorofluorene/ TIBAL (Zr/fluorene/Al=1/1/0.33);

FIG. 2

(e) (pentamethyl)cyclopentadienyltitaniumtrichloride/ TIBAL/B($C_6F_5$)$_4$CPh$_3$ (Al/B/Zr=50/1/1);

(f) (pentamethyl)cyclopentadienyltitaniumtrichloride/ MAO (Al/Zr=250);

(g) (pentamethyl)cyclopentadienyltitaniumtrichloride/ TIBAL/-1,2,3,4,5,6,7,8-octafluoro-9-(pentafluorophenyl)fluorene (Zr/fluorene/Al=1/1/50).

In the ultraviolet spectra indicated in the above FIGS. 1 and 2 the absorption peaks at 630, 640 and 920 nm, of curves (c), (d) and (f) respectively, relating to catalytic compositions according to the present invention, can be clearly distinguished. These peaks fall at much higher wave-lengths than the peaks obtained with traditional compositions based on the corresponding metallocenes activated with MAO or B($C_6F_5$)$_4$CPh$_3$.

The catalytic composition of the present invention can be basically used with excellent results in all known (co) polymerization processes of α-olefins, both in continuous and batchwise, in one or more steps, such as, for example, processes at low (0.1–1.0 MPa), medium (1.0–10 MPa) or high (10–150 MPa) pressure, at temperatures ranging from 20 to 240° C., optionally in the presence of an inert diluent. Hydrogen can conveniently be used as molecular weight regulator.

Typical α-olefins which can be (co)polymerized with the catalysts according to the present invention are aliphatic unsaturated hydrocarbons having from 2 to 30 carbon atoms, linear or branched, optionally substituted with one or more halogen atoms, such as fluorine or chlorine, whose molecule contains at least one primary unsaturated group (—CH=CH$_2$) These unsaturated hydrocarbons can also comprise cyclic groups and/or one or more additional C=C terminal or internal unsaturations, conjugated or non-conjugated with said primary unsaturated group. Examples of these α-olefins comprise ethylene, propylene, 1-butene, 4-methylpent-1-ene, 1-hexene, 1-octene, 1-decene, 1-octadecene, 1,4-hexadiene, 1,3-butadiene, ethylidene-norbornene. Ethylene is particularly preferred in both homopolymerization processes to obtain highly crystalline, high density polyethylene, and in copolymerization processes with one or more other α-olefins or with non-conjugated dienes, to obtain low density polyethylene (also called LLDPE or VLDPE) or saturated (for example EPR) or unsaturated (for example EPDM) olefinic rubbers.

These processes can be carried out in solution or suspension in a liquid diluent normally consisting of an aliphatic or cycloaliphatic saturated hydrocarbon having from 3 to 8 carbon atoms, but it can also consist of a monomer such as, for example, in the known co-polymerization process of ethylene and propylene in liquid propylene. The quantity of catalyst introduced into the polymerization mixture is preferably selected so that the concentration of metal M ranges from $10^{-5}$ to $10^{-8}$ moles/liter.

Alternatively, the polymerization can be carried out in gas phase, for example in a fluid bed reactor, normally at pressures ranging from 0.5 to 5 MPa and temperatures ranging from 50 to 150° C.

According to a particular aspect of the present invention, the catalytic composition for the (co)polymerization of α-olefins is prepared separately (preformed) by contact of components (i) and (ii), and subsequently introduced into the polymerization environment. The catalytic composition can be introduced first into the polymerization reactor followed by the reagent mixture containing the olefin or mixture of olefins to be polymerized, or the catalytic composition can be introduced into the reactor already containing the reagent mixture, or finally, the reagent mixture and the catalytic composition can be fed contemporaneously into the reactor in a typical process in continuous.

Alternatively, the three components corresponding to the compounds having formula (I), (II) and (III) respectively, can be put in contact with each other and reacted contemporaneously, in suitable proportions, and the catalytic composition thus obtained introduced into the polymerization environment.

According to another aspect of the present invention, the catalyst is formed in situ, for example by introducing components (i) and (ii) preformed, separately into the polymerization reactor containing the pre-selected olefinic monomers.

According to a different technique, which however is included in the scope of the present invention, the fluorinated cyclopentadienyl compound (A), the metallocene complex (ii) and a suitable quantity of aluminum alkyl (B) (sufficient to carry out the function of activator formation and, if necessary, alkylation of the metallocene complex), can be introduced into the polymerization environment, thus forming in situ the polymerization catalyst starting from the above initial components.

The catalysts according to the present invention can be used with excellent results in the polymerization of ethylene to give linear polyethylene and in the copolymerization of ethylene with propylene or higher α-olefins, preferably having from 4 to 10 carbon atoms, to give copolymers having various characteristics in relation to the specific polymerization conditions and the quantity and structure of the α-olefin itself. For example, linear polyethylenes with densities ranging from 0.880 and 0.940 and with molecular weights ranging from 10,000 to 2,000,000, can be obtained. α-olefins preferably used as comonomers of ethylene in the production of linear low or medium density polyethylene (known by the abbreviations ULDPE, VLDPE and LLDPE according to the density), are propylene, 1-butene, 1-hexene and 1-octene.

The catalytic composition of the present invention can also be conveniently used in copolymerization processes of ethylene and propylene to give saturated elastomeric copolymers which can be vulcanized, for example, by means of peroxides, and which are extremely resistant to aging and degradation, or in the terpolymerization of ethylene, propylene and a non-conjugated diene having from 5 to 20 carbon atoms, to obtain vulcanizable rubbers of the EPDM type. In the case of these latter processes, it has been found that the catalysts of the present invention allow polymers having a particularly high diene and average molecular weight under the polymerization conditions, to be obtained.

Preferred non-conjugated dienes for this purpose are, for example: 1,4-hexadiene and 1,6-octadiene; 5-methyl-1,4-hexadiene; 3,7-dimethyl-1,6-octadiene; 1,4-cyclohexadiene; 1,5-cyclooctadiene; 5-methylene-2-norbornene, 5-ethylidene-2-norbornene (ENB) and their mixtures.

In the case of EPDM terpolymers, the quantity of diene monomer conveniently does not exceed 15% by weight, and preferably ranges from 2 to 10% by weight. The propylene content on the other hand conveniently ranges from 20 to 50% by weight.

The catalytic composition of the present invention can also be used in homo- and co-polymerization processes of α-olefins different from ethylene, under the conditions normally adopted in the art for the corresponding polymerization processes with known catalysts based on metallocenes, to give, with excellent yields, atactic, isotactic or syndiotactic polymers, depending on the structure and geometry of the activated metallocene complex. α-olefins suitable for the purpose are those having from 3 to 20, preferably from 3 to 10, carbon atoms, optionally substituted with halogen atoms or aromatic nuclei such as, for example, propylene, 1-butene, 1-hexene, 4-methyl-1-pentene, 1-decene and styrene.

The present invention is further illustrated by the following practical examples which are purely illustrative and in no way limit the scope of the invention itself.

EXAMPLES

The following analytic and characterization techniques were used in the embodiment of the illustrative examples of the invention.

$^1$H-NMR and $^{19}$F-NMR spectroscopy, for the characterization of the molecular structures of activators, complexes and olefinic polymers, by means of a nuclear magnetic resonance spectrometer mod. Bruker MSL-300, using $CDCl_3$ as solvent, unless otherwise specified.

UV spectroscopy, for the characterization of the catalytic compositions in a solution of toluene, on a Perkin-Elmer spectrometer, mod. LAMBDA-20.

Gel-Permeation Chromatography (GPC), for the determination of the average molecular weights of the olefinic polymers Mn and Mw and the relative distribution MWD, by means of a WATERS 150-CV chromatograph with a Waters differential refractometer as detector, eluating with 1,2,4-trichlorobenzene (stabilized with Santonox) at 135° C. A set of μ-Styragel HT columns (Waters) of which three with pore dimensions of $10^3$, $10^4$, $10^5$ Å respectively, and two with pore dimensions of $10^6$ Å, establishing a flow rate of the eluant of 1 ml/min. The data were obtained and processed by means of Maxima 820 software version 3.30 (Millipore); the calculation of the number (Mn) and weight (Mw) average molecular weights was effected by means of universal calibration, selecting standards of polystyrene with molecular weights within the range of 6,500,000–2,000, for the calibration.

DSC Calorimetry, for the determination of the melting point $T_f$ and crystallization point $T_c$ of the olefinic polymers, and respective enthalpies $\Delta H_f$ and $\Delta H_c$, on a Perkin-Elmer differential calorimeter. The calorimetric curve is obtained by heating or cooling the polymeric sample at a constant rate of 10° C./min. The melting or crystallization point is determined on the curve obtained at the second scanning, under heating or cooling respectively, after subjecting the sample to a first heating or cooling cycle at 10° C./min.

The reagents and solvents used in the embodiment of the following examples are pure commercial products, unless otherwise indicated. Before use, the solvents are subjected to drying or drying distillation according to the conventional methods.

Unless otherwise indicated, all the synthesis reactions and preliminary operations of the polymerization processes, as well as the conservation and handling of the organometallic compounds, are carried out in an inert atmosphere of nitrogen or argon depending on the necessities.

Example 1

Preparation of 1,2,4-tris-(Pentafluorophenyl) cyclopentadiene (VI)

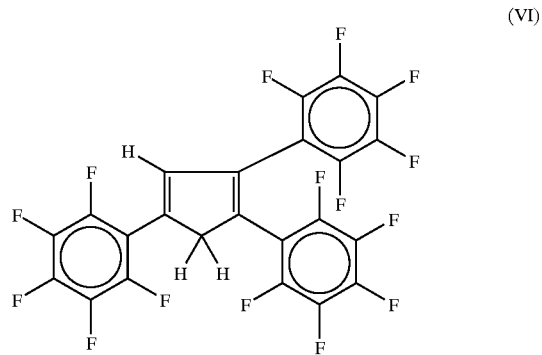

(VI)

2.6 g (0.039 moles) of cyclopentadiene are added in about 30 minutes to 100 ml of anhydrous THF containing 1.61 g (0.035 moles) of a dispersion of sodium metal at 50% in paraffin, maintained at a temperature of 20–25° C., the mixture being maintained under stirring and in an inert atmosphere. When the development of hydrogen has finished, 3.05 g (0.070 moles) of NaH are introduced as a dispersion in paraffin at 55%, together with 65 g (0.35 moles) of $C_6F_6$ and the mixture is reflux heated for 70 hours. At the end of the heating, the solvent is distilled under vacuum at 30–40° C. and the residue is washed three times with 100 ml of petroleum ether, stirring the mass vigorously. The residue is then dissolved in 50 ml of ethyl ether, 50 ml of water are added followed by 250 ml of petroleum ether. The ether phase is separated, filtered on a 5 cm layer of silica gel and then dried. 50 ml of petroleum ether are added to the semi-solid residue; a solid product is separated which is filtered. The solid obtained is crystallized from hot heptane and decoloured with carbon. After filtration and drying 1.2 g of the desired product are obtained, as a white crystalline solid.

$^1$HNMR: 4.13 ppm (s, 2H); 7.31 ppm (s, 1H); $^{19}$FNMR: −140.3 ppm (m, 4F); −140.7 ppm (m, 2F); −153.3 ppm (t, 1F); −153.8 ppm (t, 1F); −154.4 ppm (t, 1F); −160.9 ppm (quint. 4F); −162.0 ppm (t, 2F).

Example 2

Preparation of 1,2,3-tris-(Pentafluorophenyl) cyclopentadiene (VII)

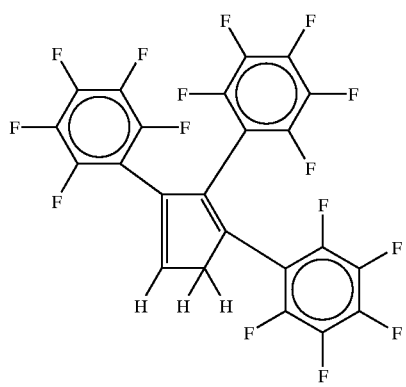

(VII)

0.2 g of 1,2,3-tris-(pentafluorophenyl)cyclopentadiene isomer are obtained, in the form of a white crystalline solid, from the crystallization mother liquor of the compound 1,2,4-tris-(pentafluorophenyl)cyclopentadiene, obtained at the end of the method of the previous example 1, after concentration and separation on a silica gel column (eluant petroleum ether).

$^1$HNMR: 3.84 ppm (d, 2H); 6.98 ppm (t, 1H); $^{19}$FNMR: −140.38 ppm (m, 4F); −140.8 ppm (m, 2F); −151.8 ppm (t, 1F); −152.9 ppm (t, 1F); −153 ppm (t, 1F); −160 ppm (m, 6F).

Example 3

Preparation of 1,2,3,4,5,6,7,8-Octafluoro-9-hydroxy-9-(2,4-bis-trifluoromethylphenyl)fluorene (VIII)

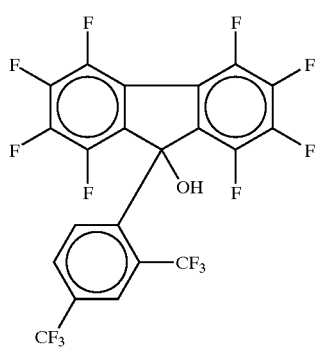

(VIII)

7 ml of butyl lithium (2.5 M) are added dropwise to a solution of 100 ml of anhydrous ethyl ether containing 5 g (0.017 moles) of 2,4-bis(trifluoromethyl)bromobenzene, cooled to −75° C. After 1 hour 3 g (0.009 moles) of 1,2,3,4,5,6,7,8-octafluorofluorenone, prepared according to the prescription indicated in the publication "Journal of the Chemical Society, part (C)", pages 2394 (1968), are added in one go. The mixture is stirred for 1 hour, is then hydrolyzed in water, the ether phase is separated, dried on Na$_2$SO$_4$ and dried. A small quantity of cold petroleum ether is added to the solid obtained which is then filtered and dried. 2.55 g of the desired pure product are obtained (yield 52.64% with respect to the octafluorofluorenone).

$^1$HNMR: 8.8 ppm (d, 1H); 8.0 ppm (d, 1H); 7.9 ppm (s, 1H); 3.0 ppm (s, 1H). $^{19}$FNMR: −58.2 ppm (s, 3F); −63.2 ppm (s, 3F); −133.3 ppm (s, 2F); −143.2 ppm (d, 2F); −150.2 ppm (s, 2F); −152.0 ppm (t, 2F).

Example 4

Preparation of 1,2,3,4,5,6,7,8-Octafluoro-9-(2,4-bis (trifluoromethylphenyl)fluorene (IX)

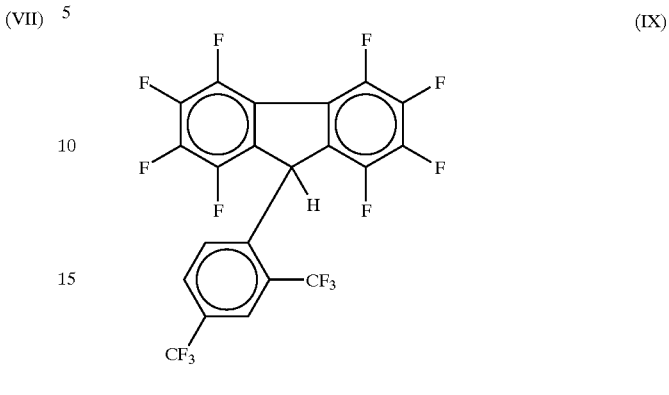

(IX)

0.95 g (0.0017 moles) of the product obtained according to the preparation of the preceeding example 3 are heated with 10 ml (0.105 moles) of PBr$_3$ to 110–120° C. for 40 minutes. The reaction mass is hydrolyzed in ice, extracted with ethyl ether, the extract is washed with an aqueous solution of NaHCO$_3$ (10%), dried on Na$_2$SO$_4$, filtered and the ether solution is dried. The residue is purified by chromatography on a silica gel column (eluant petroleum ether) obtaining, after evaporation of the pure fractions, 0.61 g of white crystalline product.

$^1$HNMR: 8.05 ppm (s, 1H); 7.6 ppm (d, 1H); 6.7 ppm (d, 1H); 5.86 ppm (s, 1H). $^{19}$FNMR: −58.3 ppm (s, 3F); −63.2 ppm (s, 3F); −133.9 ppm (d, 2F); −140.9 ppm (d, 2F); −152.3 ppm (t, 4F).

Example 5

Preparation of 1,2,3,4,5,6,7,8-Octafluoro-9-hydroxy-9-(3,5-bistrifluoromethylphenyl)fluorene (X)

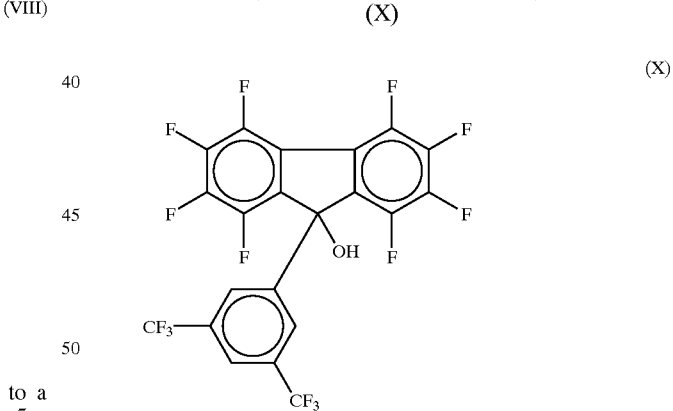

(X)

4.2 ml of Butyl lithium (1.6 M) are added, in an inert atmosphere, to an ether solution (100 ml of anhydrous solvent) of 2 g (0.0068 moles) of 3,5-bis(trifluoromethyl)-bromobenzene cooled to −75° C. At the end of the addition, the mixture is stirred for 1 h and then 1 g (0.003 moles) of 1,2,3,4,5,6,7,8-octafluorofluorenone, prepared according to the prescription specified in literature (R. D. Chambers and D. J. Spring, J. Chem. Soc. (C), 2394 (1968), is added. The mixture is stirred for 1 h, is then hydrolyzed in water, the ether phase is separated, dried on Na$_2$SO$_4$, filtered and the ether solution is dried obtaining 2.1 g of yellow product. 1.6 g of pure product (yield 99%) are obtained by separation on a silica gel column, (eluant petroleum ether/acetone (90/10)).

¹HNMR (solvent CDCl₃): 7.87 ppm (s, 1H); 7.84 ppm (s, 2H); 3.2 ppm (s, 1H). ¹⁹FNMR (solvent CDCl₃): −62.9 ppm (s, 6F); −132.6 ppm (s, 2F); −142.1 ppm (s, 2F); −149.3 ppm (s, 2F); −150.5 ppm (t, 2F).

Example 6

Preparation of 1,2,3,4,5,6,7,8-Octafluoro-9-(3,5-bis-trifluoromethylphenyl)fluorene (XI)

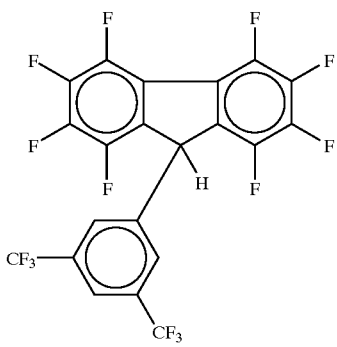

(XI)

g (0.002 moles) of the product (X), obtained according to the preparation reported in the preceeding example 5, are heated with 10 ml (0.105 moles) of PBr₃ to 110° C. for 40 minutes. The reaction mass is hydrolyzed in ice, extracted with ethyl ether, the ether extract is washed with an aqueous solution of NaHCO₃ (10%), dried on Na₂SO₄, filtered and the ether solution is dried. The residue is dissolved in 20 ml of acetic acid and 1 g of Zn in powder form is added. The mixture is stirred for 1 h at room temperature, hydrolyzed in water and then extracted with ethyl ether. The ether extract is neutralized with an aqueous solution of NaHCO₃ (10%), dried with Na₂SO₄, filtered and dried. The residue is purified on a silica gel column (eluant petroleum ether) obtaining, after evaporation of the pure fractions, 0.8 g of pure product (yield 76.6%).

¹NMR: 7.84 ppm (s, 1H); 7.53 ppm (s, 2H); 5.57 ppm (s, 1H). ¹⁹FNMR: −63 ppm (s, 6F); −133.5 ppm (s, 2F); −141.2 ppm (d, 2F); −151.9 ppm (d, 2F); −152.2 ppm (t,2F).

Example 7

Preparation of 1,2,3,4,5,6,7,8-Octafluoro-9-hydroxy-9-(pentafluorophenyl)fluorene (XII)

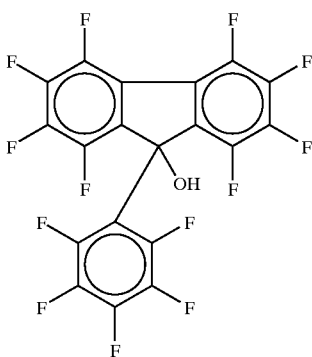

(XII)

3 ml of butyl lithium (1.6 M) are added dropwise in 15 minutes to an ether solution of 5 g (0.02 moles) of bromopentafluorobenzene (120 ml of anhydrous solvent), cooled to −75° C. The solution is stirred for 30 minutes and then 3.2 g (0.0097 moles) of 1,2,3,4,5,6,7,8-octafluorofluorenone, prepared according to the prescription specified in literature (R. D. Chambers and D. J. Spring, J. Chem. Soc. (C), 2394 (1968), are added in one go. After 30 minutes under stirring the solution is poured into water and extracted with ethyl ether. The ether solution, after drying on Na₂SO₄, is filtered and dried. 20 ml of cold petroleum ether are added to the solid obtained, which is then filtered. It is washed with a small quantity of cold petroleum ether and is then dried under vacuum. 4.6 g of white crystalline product are obtained with a yield of 93%.

¹HNMR: 3.75 ppm (t, 1H). ¹⁹FNMR: −133 ppm (d, 2F); −141 ppm (m, 2F); −143.8 ppm (d, 2F); −149.7 ppm (s, 2F); −151.4 ppm (t, 2F); −151.7 ppm (t, 1F); −159.8 ppm (m, 2F).

Example 8

Preparation of 1,2,3,4,5,6,7,8-Octafluoro-9-(pentafluorophenyl)fluorene (XIII)

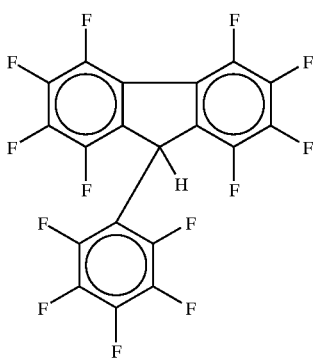

(XIII)

4.5 g (0.009 moles) of 1,2,3,4,5,6,7,8-octafluoro-9-hydroxy-9-(pentafluorophenyl)fluorene (XII), prepared as described in the preceeding example 7, are added to 25 ml (0.26 moles) of PBr₃ and heated to 110° C. for 30 minutes in an inert atmosphere. The reaction mass is hydrolyzed in ice, extracted with ethyl ether, the extract is washed with an aqueous solution (10%) of NaHCO₃, dried on sodium sulfate, filtered and dried. The residue is purified by chromatography on a silica gel column (eluant: petroleum ether/methylene chloride, 98/2), obtaining, after evaporation of the pure fractions, 3,61 g of white crystalline product (yield 84%).

¹HNMR: 5.78 ppm (s, 1H). ¹⁹FNMR: −133.8 ppm (s, 2F); −141.6 ppm (d, 1F); −142.6 ppm (d, 1F); −143.1 ppm (d, 2F); −152.1 ppm (m, 2F); −152.4 ppm (t, 1F); −152.7 ppm (t, 2F); −160.1 ppm (m, 1F); −160.7 (m, 1F).

Example 9

Preparation of 1,2,3,4,5,6,7,8-Octafluoro-9-hydroxy-9-(nonafluorodiphenyl)fluorene (XIV)

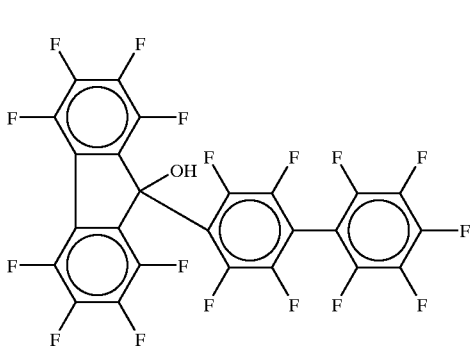

(XIV)

1.6 ml of butyl lithium (1.6 M) are added dropwise to an ether solution (50 ml of anhydrous solvent) of 1.1 g (0.0028 moles) of 2-bromononafluorodiphenyl, prepared according to the procedure described in literature (S. C. Cohen et al., Organomet. Chem., 11, 385, (1968)), cooled to −70° C. The solution is stirred for 1 h and then 0.6 g (0.0018 moles) of 1,2,3,4,5,6,7,8-octafluorofluorenone, prepared according to the prescription provided in literature (R. D. Chambers and D. J. Spring, J. Chem. Soc. (C), 2394 (1968)), are added in one go. After 1 h under stirring the solution is hydrolyzed in water and extracted with ethyl ether. The ether solution, after drying on $Na_2SO_4$, is filtered and dried. The residue is purified on a silica gel column (eluant petroleum ether/acetone, 90/10) obtaining, after evaporation of the pure fractions, 1.1 g of white product with a yield of 96%.

$^1$HNMR: 3.35 ppm (s, 1H). $^{19}$FNMR: −133 ppm (m, 2F); −133.6 ppm (m, 1F); −136.3 ppm (m, 1F); −137.9 ppm (m, 1F); −138.3 ppm (d, 1F); −141.6 ppm (m, 1F); −141.8 ppm (m, 1F); −149.9 ppm (m, 2F); −151.39 ppm (m, 3F); −152.6 ppm (t, 1F); −153.9 ppm (t, 2F); −163.3 ppm (m, 2F).

Example 10

Preparation of 1,2,3,4-Tetrakis(pentafluorophenyl)cyclopentadiene (XV)

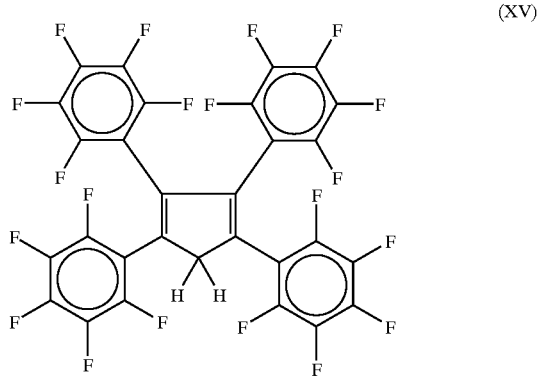

(XV)

g (4.1 mmol) of sodium hydride and 10 g of hexafluorobenzene are added to a solution of 1 g (1.77 mmoles) of 1,2,3-tris-(pentafluorophenyl)cyclopentadienyl, prepared as described in the previous example 1, in 50 ml of anhydrous THF. The reaction mixture is reflux heated for 50 h. It is then hydrolyzed in about 200 g of ice containing 5 ml of HCl 10% and is extracted with ethyl ether. The extract is dried on $Na_2SO_4$ and filtered on a 5 cm layer of granular silica. The solution is dried and the residue is separated on a silica gel column (eluant: petroleum ether/acetone=95/5). After evaporation of the pure fractions, 150 mg of the desired product are obtained as a white crystalline solid.

$^1$HNMR: 4.3 ppm (s, 2H).

Example 11

Preparation of 9,9′-bis(9H-Fluorene 1,1′,2,2′,3,3′,4,4′,5,5′,6,6′,7,7′,8,8′exadecafluoro) (XVI)

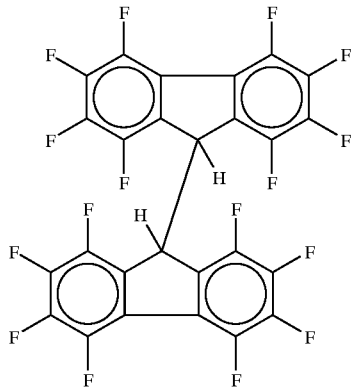

(XVI)

i) Reduction of 8F-fluorenone 2 g of octafluorofluorenone are suspended in 20 ml of acetic acid ($CH_3COOH$) and added with 1 g powdered Zinc. The mixture is stirred for 1 hour at room temperature, and complete disappearance of the starting octafluorofluorenone is detected (by TLC, eluent petroleum ether:aceton, 8:2). The reaction mixture is diluted with 150 ml of water and extracted with ethyl ether. After evaporating the solvent from the extract, 2 g of essentially pure 9-OH,9-H-octafluorofluorene are obtained (99% yield).

$^1$HNMR ($CDCl_3$) 6,16 ppm (d, 1H), 2,62 ppm (d, 1H.OH). $^{19}$FNMR ($CDCl_3$) −134,3 ppm (s, 2F), −142,5 ppm (d, 2F), −151,3 ppm (s, 2F), −152,8 ppm (t, 2F).

ii) Bromination of 9H,9-hydroxyoctafluorofluorene 2 g of 9H,9-hydroxyoctafluorofluorene, obtained as described above in step (i), are mixed with 10 ml of phosphorus-tribromide and heated at 80° C. for 1 hour. The reaction mixture is then poured on ice and extracted with ethyl ether. The ether extract is washed with water several times until neutral and dried on $Na_2SO_4$. After evaporating the solvent, 2 g of pure 9H,9Br-octafluorofluorene are obtained.

$^1$H NMR ($CDCl_3$): 6,14 ppm (s). $^{19}$F NMR −133,8 ppm (s, 2F), −137,2 ppm (t,2F), −150,5 ppm (d, 2F), −152,5 ppm (t, 2F).

iii) Dimerization

To a solution of 2 g of 9H,9Br-octafluorofluorene in 50 ml of anhydrous ethyl ether 10 ml of a 1 M ether solution of sec-butylmagnesium chloride are added. After stirring for two hours at room temperature, the reaction mixture is hydrolized with ice and extracted with about 500 ml $CH_2Cl_2$. After drying the extract with $Na_2SO_4$, the solvent is evaporated and the solid residue is dissolved with hot toluene. The solution is filtered on active carbon and celite and cooled. Solid cristals are formed, which, after filtering and drying gave 1 g of the desired 9,9′bis(9H-hexadecafluorofluorene) as a pure product.

$^1$H NMR ($CDCl_3$): 5,4 ppm (s). $^{19}$F NMR: −133,2 ppm (s, 4F), −138 to −142 ppm (m, 4F), −151,6 ppm (s, 4F), −152,7 ppm (d, 4F).

Examples 12–33

Polymerization

Polymerization tests were carried out under different conditions and using different combinations of compounds having formula (I) for the formation of the relative catalytic compositions.

General Method

Preparation of the Activating Organometallic Composition

An exactly measured quantity of 0.03 mmoles of the selected fluorinated compound having formula (I) (component A), is dissolved in about 9 ml of toluene. A quantity of triisobutylaluminum (TIBAL) is added to the solution thus obtained in order to obtain the desired molar ratio with respect to the compound having formula (I). The mixture is maintained under stirring for a few minutes and then brought to the exact volume of 10 ml, before being used in the preparation of the catalytic composition.

Preparation of the Catalytic Composition 0.03 mmoles of the selected metallocene complex are dissolved in 20 ml of toluene. 0.09 mmoles of TIBAL are added (Al/Zr=3), and the whole mixture is left under stirring for a few minutes. The solution of metallocene complex thus obtained is added to the solution of activating composition prepared as described above, in such a quantity as to obtain the molar ratio (Component A)/(metallocene) selected each time, and the mixture obtained is left under stirring for a few minutes before being used as catalytic component.

Example 12

98.5 ml of toluene containing 0.3 mmol/l of TIBAL acting as impurity scavenger, are charged into a 250 ml glass reactor equipped with a magnetic stirrer and thermostat-regulated at 30° C. The catalytic composition prepared as described above in the general methods, containing $1.5 \cdot 10^{-3}$ mmoles of 1,2-Et(Ind)$_2$ZrCl$_2$ and $1.5 \cdot 10^{-3}$ mmoles of 1,2,3-tris(pentafluorophenyl)cyclopentadiene, prepared as described in the previous example 2, with a molar ratio (Component A)/Zr=1 and a molar ratio (total Al/(Component A)=3.5, is then introduced. The reactor is pressurized at 50 Kpa (rel.) with ethylene and the mixture is maintained under stirring for 60 minutes, continuously feeding ethylene to keep the pressure constantly at the initial value. At the end the reactor is depressurized and 5 ml of methanol are introduced to terminate the polymerization and deactivate the catalyst. The polymer is recovered by precipitation in 400 ml of methanol acidified with hydrochloric acid, filtration and drying under vacuum at 40° C. for about 8 hours. 0.5 g of polyethylene are obtained.

Example 13

The same procedure is adopted as in the previous example 12, but using $1.5 \cdot 10^{-3}$ mmoles of 1,2,4-tris-(pentafluorophenyl)cyclopentadiene (prepared according to the previous example 1) instead of 1,2,3-tris(pentafluorophenyl)cyclopendadiene. 0.4 g of polyethylene are obtained.

Example 14

The same procedure is adopted as in example 12, but using $3.0 \cdot 10^{-3}$ mmoles of 1,2,4,5-tetrakis-(pentafluorophenyl)cyclopentadiene (prepared according to the previous example 10) instead of $1.5 \cdot 10^{-3}$ mmoles of 1,2,3-tris-(pentafluorophenyl)cyclopentadiene with a molar ratio Al/(Component A)=3.5 and a molar ratio Zr/Activator=0.5. 0.8 g of polyethylene are obtained.

Example 15

The same procedure is adopted as in example 12, but using $1.5 \cdot 10^{-3}$ mmoles of 1,2,3,4,5,6,7,8-octafluoro-9-(3,5-bis-trifluoromethylphenyl)fluorene (prepared according to the previous example 6) instead of 1,2,3-tris(pentafluorophenyl)cyclopendadiene with a molar ratio Al/(Component A)=5. 1.15 g of polyethylene are obtained.

Example 16

The same procedure is adopted as in example 12, but using $1.9 \cdot 10^{-3}$ mmoles of 1,2,3,4,5,6,7,8-octafluoro-9-(pentafluorophenyl)fluorene (prepared according to the previous example 8) instead of $1.5 \cdot 10^{-3}$ mmoles of 1,2,3-tris(pentafluorophenyl)cyclopendadiene, with a molar ratio Al/(Component A)=3.3 and a molar ratio Zr/(Component A)=0.8. 1.2 g of polyethylene are obtained.

Example 17 (Comparative)

The same equipment and the same conditions are adopted as in example 12 above, but using a traditional catalytic system of the ionic type. Consequently, $1.5 \cdot 10^{-3}$ mmoles of 1,2-Et(Ind)$_2$ZrCl$_2$ are dissolved in 1 ml of toluene and 0.015 mmoles of triisobutylaluminum are added to this solution as alkylating agent, the mixture being left under stirring for 15 minutes. This mixture is added to a solution of $1.5 \cdot 10^{-3}$ mmoles of B(C$_6$F$_5$)$_4$PhNHMe$_2$ in 1 ml of toluene and the whole mixture is left under stirring for a few minutes. The resulting catalytic composition (comparative) is charged into the 250 ml glass reactor, which is pressurized at 50 Kpa (rel.) with ethylene and the same procedure is adopted as in example 12. At the end, 1.1 g of polyethylene are obtained.

Example 18

98.5 ml of toluene containing 1 mmole/l of TIBAL acting as impurity scavenger, are charged into a 250 ml glass reactor equipped with a magnetic stirrer and thermostat-regulated at 80° C. The catalytic composition, prepared apart as described above in the general methods, containing $1.5 \cdot 10^{-3}$ mmoles of 1,2-Et(Ind)$_2$ZrCl$_2$ and $3.0 \cdot 10^{-3}$ mmoles of 1,2,3,4,5,6,7,8-octafluoro-9-hydroxy-9-(pentafluorophenyl)-fluorene (as component A), prepared as described in the previous example 7, with a molar ratio (Component A)/Zr=2 and a molar ratio (total Al/(Component A)=2.7, is then introduced. The reactor is pressurized at 50 Kpa (rel.) with ethylene and the mixture is maintained under stirring for 60 minutes at 80° C., continuously feeding ethylene to keep the pressure constantly at the initial value. At the end the reactor is depressurized and 5 ml of methanol are introduced to terminate the polymerization and deactivate the catalyst. The polymer is recovered by precipitation in 400 ml of methanol acidified with hydrochloric acid, filtration and drying under vacuum at 40° C. for about 8 hours. 10 g of polyethylene are obtained, having Mw=114000, Mn=47200, MWD=2.4; $T_f$=132.98° C., $\Delta H_f$=−194.34 J/g, $T_c$=114.22° C., , $\Delta H_c$=−197.52 J/g.

Example 19

The same procedure is adopted as in example 18, using the same molar quantity of 1,2,3,4,5,6,7,8-octafluoro-9-

(pentafluorophenyl)fluorene, prepared as described in the previous example 8, instead of 1,2,3,4,5,6,7,8-octafluoro-9-(hydroxypentafluorophenyl)fluorene. 10.5 g of polyethylene are obtained, with Mw=88250, Mn=42270, MWD=2.08; $T_f$=132.6° C., $\Delta H_f$=203.7 J/g, $T_c$=113.54° C., , $\Delta H_c$=−205.33 J/g.

Example 20

The same procedure is adopted as in example 18, using however 7.5·10$^{-3}$ mmoles of 1,2,3,4,5,6,7,8-octafluoro-9-(2,4-bis-trifluoromethylphenyl)fluorene, prepared as described in the previous example 4, instead of 3.0·10$^{-3}$ mmoles of 1,2,3,4,5,6,7,8-octafluoro-9-hydroxy-9-(pentafluorophenyl)fluorene, with a molar ratio Component A/Zr=5.0 and a molar ratio $Al_{total}$/(component A)=1.6. At the end 7.5 g of polyethylene are obtained.

Example 21

The same procedure is adopted as in example 18, but using the same molar quantity of 1,2,3,4,5,6,7,8-octafluoro-9-hydroxy-9-(3,5-bis-trifluoromethylphenyl)fluorene instead of 1,2,3,4,5,6,7,8-octafluoro-9-hydroxy-9-(pentafluorophenyl)fluorene. 6 g of polyethylene are obtained.

Example 22 (Comparative)

The same equipment and the same conditions are adopted as in example 18 above, but using a traditional catalytic system of the ionic type. Consequently, 1.5·10$^{-3}$ mmoles of 1,2-Et(Ind)$_2$ZrCl$_2$ are dissolved in 1 ml of toluene and 0.015 mmoles of triisobutylaluminum are added to this solution as alkylating agent, the mixture being left under stirring for 15 minutes. This mixture is added to a solution of 1.5·10$^{-3}$ mmoles of B(C$_6$F$_5$)$_4$Ph$_3$C in 1 ml of toluene and the whole mixture is left under stirring for a few minutes. The resulting catalytic composition (comparative) is charged into the 250 ml glass reactor preheated to 80° C. and pressurized at 50 Kpa (rel.) with ethylene and the same procedure is adopted as in example 17. At the end, 9.6 g of polyethylene are obtained, with Mw=56000, Mn=23100, MWD=2.4; $T_f$=130.05° C., $\Delta H_f$=214.09 J/g, $T_c$=112.95° C., , $\Delta H_c$=−218.7 J/g.

Example 23

500 ml of toluene containing 0.72 mmoles/l of TIBAL acting as impurity scavenger, are charged into a 1 liter AISI steel reactor equipped with a mechanical blade stirrer. The reactor is thermostat-regulated at 80° C. and the catalytic composition, prepared apart as described above in the general methods, containing 1.5·10$^{-3}$ mmoles of 1,2-Et(Ind)$_2$ZrCl$_2$ and 1.5·10$^{-3}$ mmoles of 1,2,3,4,5,6,7,8-octafluoro-9-(pentafluorophenyl)fluorene (as component A), prepared as described in the previous example 8, with a molar ratio (Component A)/Zr=1 and a molar ratio (total Al/(Component A)=4, is then introduced. The reactor is pressurized at 0.80 MPa (rel.) with ethylene and the mixture is maintained under stirring for 60 minutes at 80° C., continuously feeding ethylene to keep the pressure constantly at the initial value. At the end the reactor is depressurized and 5 ml of methanol are introduced to terminate the polymerization and deactivate the catalyst. The polymer is recovered by precipitation in 1000 ml of methanol acidified with hydrochloric acid, filtration and drying under vacuum at 40° C. for about 8 hours. 78 g of polyethylene are obtained, having Mn=47800, Mw=88500, MWD=1.85.

Example 24

The same procedure is adopted as in example 23, but using the same molar quantity of 1,2,3,4,5,6,7,8-octafluoro-9-hydroxy-9-(pentafluorophenyl)fluorene, prepared according to example 7, instead of 1,2,3,4,5,6,7,8-octafluoro-9-(pentafluorophenyl)fluorene. 79.2 g of polyethylene are obtained, having Mn=47350, Mw=110560, MWD=2.3.

Example 25

The same procedure is adopted as in example 23, but using 1,2,3,4,5,6,7,8-octafluoro-9-(3,5-bis-trifluoromethylphenyl)fluorene, prepared according to example 6, instead of 1,2,3,4,5,6,7,8-octafluoro-9-(pentafluorophenyl)fluorene. 74 g of polyethylene are obtained, with Mw=46000, Mn=80000, MWD=1.73; $T_f$=137° C., $\Delta H_f$=216.3 J/g, $T_c$=110.5° C., , $\Delta H_c$=−206.45 J/g.

Example 26

The same procedure is adopted as in example 23, but using as fluorinated compound 4.5·10$^{-3}$ mmoles of 1,2,3,4,5,6,7,8-octafluorofluorene, prepared according to the method described in the publication "Journal of Organic Chemistry", vol. 45 (1980), page 1290, instead of 1.5·10$^{-3}$ mmoles of 1,2,3,4,5,6,7,8-octafluoro-9-(pentafluorophenyl)fluorene, with a molar ratio (component A)/Zr=3 and a molar ratio Al/(component A)=4. 66.8 g of polyethylene are obtained having Mn=50600, Mw=111200, MWD=2.19.

Example 27

The same procedure and same ratios between the catalytic components are adopted as in example 25, but using 1,2,3,4,5,6,7,8-octafluoro-9-hydroxy-9-(nonafluorophenyl)fluorene, prepared according to the previous example 9, instead of 1,2,3,4,5,6,7,8-octafluorofluorene. 66.8 g of polyethylene are obtained, having Mn 45100, Mw=85800, MWD=1.9.

Example 28 (Comparative)

The same equipment and same conditions are adopted as in the previous example 23, but using the same traditional catalytic system of the ionic type as the previous example 22 (comparative). 76.6 g of polyethylene are obtained.

Example 29

30 ml of toluene are charged into a 100 ml glass reactor equipped with a magnetic stirrer. The reactor is thermostat-regulated at 30° C. 1.5·10$^{-3}$ mmoles of 1,2-Ethylenebis(4,5,6,7-tetrahydroindenyl)zirconiumdimethyl-(Et(THInd)$_2$ZrMe$_2$) are dissolved in 10 ml of toluene, and this solution is added to a toluene solution with a volume of 10 ml containing 1.5·10$^{-3}$ mmoles of 1,2,3,4,5,6,7,8-octafluoro-9-(pentafluorophenyl)fluorene and 1.5·10$^{-3}$ mmoles of TIBAL, the whole mixture being left under stirring for a few minutes (molar ratio Zr/(component A)/TIBAL=1/1/1). The resulting catalytic mixture is charged into the reactor which is pressurized at 50 KPa (rel.) with ethylene and the mixture is maintained under stirring for 60 minutes at 30° C., continuously feeding ethylene to keep the pressure constantly at the initial value. At the end the reactor is depressurized and 5 ml of methanol are introduced to terminate the polymerization and deactivate the catalyst. The polymer is recovered by precipitation in 200 ml of methanol acidified with hydrochloric acid, filtration and drying under vacuum at 40° C. for about 8 hours. 0.65 g of polyethylene are obtained.

Example 30 (Comparative)

The same procedure is adopted as in the previous example 29, but using as catalytic composition a traditional ionic catalyst prepared by the reaction of $1.5 \cdot 10^{-3}$ mmoles of $Et(THInd)_2ZrMe_2$ with $1.5 \cdot 10^{-3}$ mmoles of $CPh_3B(C_6F_5)_4$ in toluene (molar ratio Zr/B=1). 0.7 g of polyethylene are obtained.

Example 31

98.5 ml of toluene containing 1.1 mmoles/l of TIBAL, as impurity scavenger, and 2.5 g of 1-hexene are charged into a 250 ml glass reactor. The reactor is thermostat-regulated at 50° C. and 1.5 ml of the catalytic solution prepared according to the general procedure described above, containing $1.5 \cdot 10^{-3}$ mmoles of $1,2\text{-}Et(Ind)_2ZrCl_2$ and, as component A, $1.5 \cdot 10^{-3}$ mmoles of 1,2,3,4,5,6,7,8-octafluoro-9-(pentafluorophenyl)fluorene, with a molar ratio Zr/(component A)=1 and with a molar ratio $(Al_{total})$/(component A)=1. The reactor is pressurized at 50 KPa (rel.) with ethylene and the same procedure is adopted as in the previous examples. At the end, 7 g of ethylene/hexene copolymer (hexene content in the polymer=16% moles) are obtained.

Example 32 (Comparative)

The same procedure is adopted as in the previous example 31, but using as catalytic composition a traditional ionic catalyst prepared by the reaction of $1.5 \cdot 10^{-3}$ mmoles of $Et(THInd)_2ZrMe_2$ with $1.5 \cdot 10^{-3}$ mmoles of $CPh_3B(C_6F_5)_4$ in toluene (molar ratio Zr/B=1). At the end of the polymerization, 8.5 g of ethylene/hexene copolymer (hexene content in the polymer 17% moles), are obtained.

Example 33

The following products are charged in order into a 25 ml glass reactor, equipped with a magnetic stirrer: 6.7 ml of toluene, 0.03 mmoles of (pentamethylcyclopentadienyl)-titaniumtrichloride ($Cp^*TiCl_3$), 3 mmoles of TIBAL and 0.03 mmoles of 1,2,3,4,5,6,7,8-octafluoro-9-(pentafluorophenyl)-fluorene (molar ratio Ti/Al/(component A)=1:1:1). The mixture is heated to 65° C. for 15 minutes, and 6.9 ml (60 mmoles) of styrene, previously purified by distillation at reduced pressure on NaH are then added (molar ratio styrene/Ti=2000). After 60 minutes the polymerization is interrupted by the addition of 30 ml of methanol acidified with 10% of HCl. The polymer is recovered by filtration and drying under vacuum at 80° C. for about 48 hours. 3.5 g of polystyrene are obtained.

Example 34 (High Temperature Polymerization)

A polymerization test is carried out in a 1 liter adiabatic steel reactor, capable of operating at up to 100 MPa and at temperatures ranging from 160 to 220° C. Two streams, containing the monomers and the catalyst solution, respectively, are fed to the reactor, the flow-rates being maintained at such a value as to allow a residence time of about 45 seconds. The conversion per passage, and consequently the temperature, is controlled and regulated by means of the flow-rate of the catalyst solution, in order to maintain a production of polymer within the range of 3–4 kg/h. The catalyst solution is prepared by dissolving 550 mg (1.14 mmoles) of the complex o-benzylidene-bis-($\eta^5$-1-indenyl)zirconium dichloride, prepared according to example 1 of patent application Nr. MI98-A00479, in 211 ml of toluene and by adding 552.2 mg (1.16 mmoles) of 1,2,3,4,5,6,7,8-octafluoro-9-(pentafluorophenyl)fluorene (molar ratio (component A)/Zr=about 1) and 116 mmoles equal to 29 ml of TIBAL (also comprising the quantity of TIBAL necessary as scavenger). This solution is maintained under stirring at room temperature for about 30 minutes and then diluted by adding 1800 ml of Isopar-L before introduction into the reactor. The concentration of Zr into the solution fed is 0.57 mM. The stream containing the monomers consists of ethylene 64% by volume and 1-butene 46%. The polymerization temperature is kept constant at around 160° C. and the pressure is set at 80 MPa. Under these conditions, an ethylene-butene copolymer (LLDPE) is obtained having the following characteristics: Mn=38000, Mw=102000, MWD=2.6 MFI=0.5 g/10 min, density= 0.9208 g/cm³ Short Chain Branching number=8.3/(1000 C), Melting point=118.4° C.

The catalytic activity proved to be 9200 kg/g Zr.

What is claimed is:

1. An organometallic composition comprising the reaction product between:

(A) a fluorinated organic compound of formula (I):

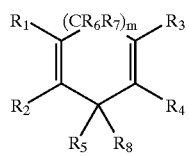

(I)

wherein each $R_1$ to $R_7$ group is a substituent independently selected from the group consisting of hydrogen, fluorine, a fluorinated or non-fluorinated, aliphatic hydrocarbyl group and a fluorinated or non-fluorinated aromatic hydrocarbyl group, having from 1 to 20 carbon atoms, optionally joined to a different hydrocarbyl group to form a further cycle, on the condition that at least two of the groups $R_1$ to $R_5$ are independently selected from the group consisting of:

fluorine, a fluorinated alkyl group having the formula —CF$(R_9R_{10})$, wherein each $R_9$ or $R_{10}$ group is a substituent independently selected from the group consisting of hydrogen, fluorine, a fluorinated or non-fluorinated, aliphatic hydrocarbyl group and a fluorinated or non-fluorinated aromatic hydrocarbyl group, having from 1 to 20 carbon atoms, optionally joined to a different hydrocarbyl group to form a further cycle and at least one of them is fluorine, or fluorinated alkyl at least in position 1, or a fluorinated aryl $Ar_F$ as defined below, or a fluorinated vinyl group $V_F$ as defined below, or a fluorinated aryl group $Ar_F$ substituted on the aromatic ring with at least two groups selected from fluorine, a —CF$(R_9R_{10})$ group as defined above or a different $Ar_F$ group, or a fluorinated vinyl group $V_F$ substituted on at least two positions of the double bond with groups selected from the group consisting of fluorine, a —CF$(R_9R_{10})$ group and an $Ar_F$ group as defined above;

the $R_8$ group is hydrogen, —OH, —SH, or, together with the $R_5$ group forms a carbonyl oxygen; and m is 0 or 1;

(B) an organometallic compound of formula (II)

$$M'R_nX_{(p-n)} \quad (II)$$

wherein M' is a metal of group 2 or 13 of the periodic table of elements; each R is independently a hydrocarbyl group having from 1 to 10 carbon atoms; each X is a halogen atom; p is 2 for group 2 and 3 for group 13, n is a decimal number ranging from 1 to p.

2. The organometallic composition according to claim 1, wherein M' is Mg or Al and X is chlorine or bromine.

3. The composition according to claim 1, wherein M' is Al, p=n=3 and R is alkyl.

4. The composition according to claim 1, wherein m is zero.

5. The composition according to claim 1, wherein $R_5$ is fluorine or fluorinated aryl.

6. The composition according to claim 1, wherein $R_8$ is hydrogen.

7. The composition according to claim 1, wherein $R_8$ is a hydroxy group.

8. The composition according to claim 1, wherein said fluorinated organic compound has formula (IV):

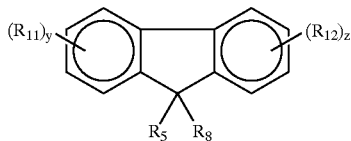

wherein
$R_5$ and $R_8$ have the same meaning as defined for formula (I),
y and z independently range from 1 to 4,
$R_{11}$ and $R_{12}$ are independently selected from the group consisting of fluorine, a fluorinated or non-fluorinated aliphatic hydrocarbyl group and a fluorinated or non-fluorinated aromatic hydrocarbyl group, having from 1 to 20 carbon atoms, optionally joined to a different $R_{11}$ or $R_{12}$ hydrocarbyl group, respectively, to form another cycle,
on the condition that at least 3 of the groups $R_5$, $R_{11}$ and $R_{12}$ are independently selected from the group consisting of:
fluorine,
a fluorinated alkyl group having the formula —CF($R_9R_{10}$) wherein each $R_9$ or $R_{10}$ group has any of the above meanings of $R_1$ to $R_7$ groups of claim 1 and at least one of these is fluorine, or fluorinated alkyl at least in position 1, or a fluorinated aryl $Ar_F$ as defined below, or a fluorinated vinyl group $V_F$ as defined below, or
a fluorinated aryl $Ar_F$ substituted on the aromatic ring with at least two groups selected from the group consisting of fluorine, a —CF($R_9R_{10}$) group as defined above and a different $Ar_F$ group, or
a fluorinated vinyl group $V_F$ substituted on at least two positions of the double bond with groups selected from the group consisting of fluorine, a —CF($R_9R_{10}$) group and an $Ar_F$ group as defined above in claim 1.

9. The composition according to claim 8, wherein all eight $R_{11}$ and $R_{12}$ are the same and are trifluoromethyl or fluorine.

10. The composition according to claim 1, wherein components (A) and (B) are in such a quantity that the ratio between M' and said compound of formula (I) ranges from 0.1 to 100.

11. A catalytic composition comprising the following components in contact with each other:
(i) the organometallic composition according to claim 1,
(ii) a metallocene complex of a metal M of group 4 of the periodic table, comprising at least one cyclopentadienyl group, optionally substituted, pentahapto($\eta^5$-) coordinated to said metal.

12. The catalytic composition according to claim 11, wherein said components (i) and (ii) are in such a quantity that the molar ratio (A)/(M), wherein (M) are the moles of metal in component (ii) and (A) the moles of di-unsaturated compound in the organometallic composition (i), ranges from 0.5 to 50.

13. The catalytic composition according to claim 11, wherein said metallocene complex (ii) has the following formula (III):

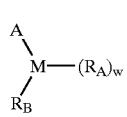

wherein:
M represents a metal selected from the group consisting of Ti, Zr and Hf;
each $R_A$ independently represents an anionic group bound to the metal M, different from cyclopentadienyl or substituted cyclopentadienyl;
w is an integer of 1 or 2, depending on whether the valence of M is 3 or 4;
A represents an anionic ligand having from 5 to 30 carbon atoms comprising an $\eta^5$-cyclopentadienyl ring coordinated to the metal M;
$R_B$, regardless of the nature of the other substituents, has any of the meanings previously specified for the ligand A and for the group $R_A$, and can also be connected with said group A by means of a divalent organic group having from 1 to 15 carbon atoms, to form a bridged metallocene complex.

14. The catalytic composition according to claim 13, wherein, in said metallocene complex having formula (III), the groups $R_A$ and $R_B$ are independently selected from the group consisting of hydride, chloride, bromide, a hydrocarbyl or halogenated hydrocarbyl radical, different from cyclopentadienyl, having from 1 to 30 carbon atoms, a phosphonate, sulfonate or carbonate group, an alkoxy, carboxy or aryloxy group having from 1 to 20 carbon atoms, an amide group, an organic group having from 1 to 20 carbon atoms bound to the metal M with an amide nitrogen atom, and an organic group having from 1 to 20 carbon atoms, bound to the metal M with a silicon atom.

15. The catalytic composition according to claim 11, wherein said metallocene complex (ii) has the following formula (V):

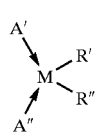

wherein:
M represents a metal selected from the group consisting of titanium, zirconium and hafnium;

A' and A" independently represent an anionic group containing an η⁵-cyclopentadienyl ring coordinated to the metal M;

R' and R" independently is selected from the group consisting of hydride, chloride, bromide, a $C_1$–$C_{20}$ alkyl or alkylaryl group, a $C_3$–$C_{20}$ alkylsilyl group, a $C_5$–$C_{20}$ cycloalkyl group, a $C_6$–$C_{20}$ aryl or arylalkyl group, a $C_1$–$C_{20}$ alkoxyl or thioalkoxyl group, a $C_2$–$C_{20}$ carboxylate or carbamate group, a $C_2$–$C_{20}$ dialkylamide group and a $C_4$–$C_{20}$ alkylsilylamide group.

16. The catalytic composition according to claim 15, wherein, in said metallocene complex having formula (V), the groups A' and A" are cyclopentadienyl, indenyl, or fluorenyl, wherein one or more carbon atoms of their molecular skeletons are substituted with a linear or branched, alkyl, aryl or alkylsilyl radical having from 1 to 10 carbon atoms.

17. A method for the preparation of the catalytic composition according to claim 13, comprising putting components (i) and (ii) in contact with each other, so that the ratio (A)/(M), wherein (M) are the moles of metallocene complex having formula (III) and (A) the moles of fluorinated compound having formula (I) in claim 1, ranges from 0.5 to 50.

18. The method according to claim 17, wherein said components (i) and (ii) are put in contact and reacted with each other in an inert diluent and at temperatures ranging from room temperature up to 150° C., for times varying from 1 to 30 minutes.

19. The method according to claim 17, wherein said metallocene complex in component (ii) consists of a complex having formula (III) wherein $R_A$ and $R_B$ are both different from alkyl, comprising the step of reacting said metallocene complex with a quantity of said organometallic compound having formula (II) sufficient to effect the alkylation of said metallocene complex.

20. The method according to claim 19, wherein the metal M' in the compound having formula (II) is Mg and the atomic ratio M'/M ranges from 3 to 10.

21. A process for the (co)polymerization of one or more α-olefins, both in continuous and batch, in one or more steps in suitable reactors, at 0.1–1.0 MPa, 1.0–10 MPa or 10–150 MPa pressure, at temperatures ranging from 20 to 240° C., optionally in the presence of an inert diluent, wherein said one or more α-olefins are (co)polymerized, under one of the above conditions, in the presence of a catalytic composition according to claim 11.

22. The process according to claim 21, wherein ethylene is co-polymerized with at least one α-olefin having from 3 to 10 carbon atoms.

23. The process according to claim 22, wherein, in addition to said at least one α-olefin, an aliphatic or alicyclic, non-conjugated diene having from 5 to 20 carbon atoms, is copolymerized with ethylene.

24. The process according to 21, wherein said process is carried out in a solution or suspension in a suitable inert liquid medium consisting of an aliphatic or cycloaliphatic hydrocarbon having from 3 to 15 carbon atoms, or a mixture of these.

25. The process according to claim 21, wherein said catalytic composition is prepared separately and subsequently put in contact with said one or more α-olefins.

26. The process according to claim 21, wherein said catalytic composition is prepared in situ in said process.

27. The composition according to claim 1, wherein components (A) and (B) are in such a quantity that the ratio between M' and said compound of formula (I) or (IV) ranges from 1 to 10.

28. The composition according to claim 8, wherein at least 4 of the groups $R_5$, $R_{11}$ and $R_{12}$ are independently selected from the group consisting of:

fluorine, a fluorinated alkyl group having the formula —CF($R_9R_{10}$) wherein each $R_9$ or $R_{10}$ group can have any of the above meanings of $R_1$ to $R_7$ groups of claim 1 and at least one of these is fluorine, or fluorinated alkyl at least in position 1, or a fluorinated aryl $Ar_F$ as defined below, or a fluorinated vinyl group $V_F$ as defined below, or a fluorinated aryl $Ar_F$ substituted on the aromatic ring with at least two groups selected from the group consisting of fluorine, a —CF($R_9R_{10}$) group as defined above and a different $Ar_F$ group, or a fluorinated vinyl group $V_F$ substituted on at least two positions of the double bond with groups selected from the group consisting of fluorine, a —CF($R_9R_{10}$) group and an $Ar_F$ group as defined above.

29. The composition according to claim 1, wherein at least three of the groups $R_1$ to $R_5$ are independently selected from the group consisting of:

fluorine, a fluorinated alkyl group having the formula —CF($R_9R_{10}$), wherein each $R_9$ or $R_{10}$ group has any of the above meanings of the $R_1$ to $R_7$ groups in claim 1 and at least one of them is fluorine, or fluorinated alkyl at least in position 1, or a fluorinated aryl $Ar_F$ as defined below, or a fluorinated vinyl group $V_F$ as defined below, or a fluorinated aryl group $Ar_F$ substituted on the aromatic ring with at least two groups selected from the group consisting of fluorine, a —CF($R_9R_{10}$) group as defined above and a different $Ar_F$ group.

30. The composition according to claim 8, wherein all eight $R_{11}$ and $R_{12}$ are the same and are fluorine.

* * * * *